(12) United States Patent
Barber (10) Patent No.: US 9,486,430 B2
(45) Date of Patent: Nov. 8, 2016

(54) TREATMENT OF NEURODEGENERATIVE DISEASE

(76) Inventor: Elizabeth K. Barber, Winfield, IL (US)

(*) Notice: Subject to any disclaimer, the term of this patent is extended or adjusted under 35 U.S.C. 154(b) by 0 days.

(21) Appl. No.: 13/451,778

(22) Filed: Apr. 20, 2012

(65) Prior Publication Data

US 2012/0263698 A1    Oct. 18, 2012

Related U.S. Application Data

(63) Continuation-in-part of application No. PCT/US2011/057544, filed on Oct. 24, 2011.

(60) Provisional application No. 61/470,519, filed on Apr. 1, 2011, provisional application No. 61/470,608, filed on Apr. 1, 2011, provisional application No. 61/405,987, filed on Oct. 22, 2010.

(51) Int. Cl.
| | |
|---|---|
| A61K 31/385 | (2006.01) |
| A61K 31/198 | (2006.01) |
| A61K 31/05 | (2006.01) |
| A61K 38/06 | (2006.01) |
| A61K 31/122 | (2006.01) |
| A61K 31/205 | (2006.01) |
| A61K 31/685 | (2006.01) |
| A61K 33/06 | (2006.01) |

(52) U.S. Cl.
CPC ............. *A61K 31/198* (2013.01); *A61K 31/05* (2013.01); *A61K 31/122* (2013.01); *A61K 31/205* (2013.01); *A61K 31/385* (2013.01); *A61K 31/685* (2013.01); *A61K 33/06* (2013.01); *A61K 38/063* (2013.01)

(58) Field of Classification Search
CPC . A61K 31/385; A61K 31/685; A61K 31/106
See application file for complete search history.

(56) References Cited

U.S. PATENT DOCUMENTS

| | | | | |
|---|---|---|---|---|
| 2006/0099244 | A1* | 5/2006 | Guilford | 424/450 |
| 2010/0080762 | A1* | 4/2010 | Goralczyk | 424/59 |

FOREIGN PATENT DOCUMENTS

WO    WO 2009003147 A1 * 12/2008

OTHER PUBLICATIONS

Nunes et al. "Pharmacokinetics of Trans-resveratrol Following Repeated Administration in Healthy Elderly and Young Subjects". (Oct. 1, 2009) Journal of Clinical Pharmacology vol. 49: 1477-1482.*
Henchcliffe et al. "Mitrochondrial biology and oxidatvie stress in Parkinson disease pathogenesis." (2008) Nature Clinical Practice: Neurology vol. 4: 600-609.*
Jin et al. "Neuroprotective effect of resveratrol on 6-OHDA-induced Parkinson's disease in rats." (2008) European Journal of Pharmacology, vol. 600: 78-82.*
The Parkinson Study Group, "Levodopa and the Progression of Parkinson's Disease" (2004) New England Journal of Medicine, vol. 351: 2498-2508.*
Almeida et al. "Pharmacokinetic and safety profile of trans-resveratrol in a rising multiple-dose study in healthy volunteers." (2009) Molecular and Nutritional Food Research vol. 53: s7-s15.*
Haataja L, Gurlo T, Huang CJ, Butler PC. Islet amyloid in type 2 diabetes, and the toxic oligomer hypothesis. Endocrine Reviews 2008; 29: 303-16.
Höppener JW, Ahrén B, Lips CJ. Islet amyloid and type 2 diabetes mellitus. NEJM 2000; 343: 411-9.
Irvine GB, El-Agnaf OM, Shankar GM, Walsh DM. Protein aggregation in the brain: the molecular basis for Alzheimer's and Parkinson's diseases. Molecular Medicine (Cambridge, Mass.) 2008; 14: 451-64.
More than just mad cow disease, Nature Structural Biology 2001; 8: 281.
Truant R, Atwal RS, Desmond C, Munsie L, Tran T . Huntington's disease: revisiting the aggregation hypothesis in polyglutamine neurodegenerative diseases. The FEBS J 2008; 275: 4252-62.
Weydt P, La Spada AR. Targeting protein aggregation in neurodegeneration—lessons from polyglutamine disorders. Exp Op on Ther Tar 2006; 10: 505-13.
Speranza, VD. Amyloid. From: Baethge BA and Jacobsen DR, Amyloidosis. In: Histologic Preparations. Common Problems and their Solutions, Brown RX, ed. National Society of Histotechnology/CAP, 2009.
Dotti CG and De Strooper B. Alzheimer's dementia by circulation disorders: when trees hide the forest. Nat Cell Biol 2009; 11: 114-6.
Sipe JD, Benson MD, Buxbaum JN, et al. Amyloid fibril protein nomenclature: 2010 recommendations from the nomenclature committee of the International Society of Amyloidosis. Amyloid 2010; 17: 101-104.
The Parkinson Study Group. A controlled trial of rasagiline in early Parkinson disease. The TEMPO study. Arch Neurol. 2002, 59(12): 1937-1943.

(Continued)

Primary Examiner — Robert Yamasaki
Assistant Examiner — Teresa E Knight (57) ABSTRACT

A method for reducing alpha-synuclein amyloid protein in a patient suffering from Parkinson's Disease comprising administering to the patient an effective amount of trans-resveratrol, a method for treating a neurodegenerative disease associated with amyloid proteins comprising administering to a patient in need thereof an effective amount of trans-resveratrol, and a method for treating Parkinson's Disease comprising administering to a patient in need thereof a pharmaceutically effective amount of carbidopa, levodopa, and trans-resveratrol are described. More particularly, the effect of trans-resveratrol on reducing the pharmaceutically effective dose of at least one of carbidopa and levodopa in the treatment of Parkinson's Disease is described. In addition, a method of improving cognition, speech and/or movement in a patient suffering from Parkinson's Disease comprising administering to the patient carbidopa, levodopa and trans-resveratrol is described.

3 Claims, 3 Drawing Sheets

(56) References Cited

OTHER PUBLICATIONS

Parkinson Study Group. DATATOP: A multicenter controlled clinical trial in early Parkinson's disease. Arch Neurol. 1989; 46:1052-1060.

Parkinson Study Group. Effect of Deprenyl on the progression of disability in early Parkinson's disease. N. Engl. J. Med. 1989; 321:1364-1371.

Mytilineou C, Leonarki EK, Radcliffe P, et al. Deprenyl and desmethylselegiline protect mesencephalic neurons from toxicity induced by glutathione depletion. J Pharmacol Exp Ther. 1998:284: 700-706.

Tatton WG, Ju WY, Holland DP, et al. (−)-Deprenyl reduces PC12 cell apoptosis by inducing new protein synthesis. J Neurochem. 1994; 63: 1572-1575.

Talton WG, Ju WYH, Wadia J, et al., Reduction of neuronal apoptosis by small molecules: promise for new approaches to neurological therapy. In: Olanow EW, Jenner P, Youim MHB eds. Neurodegeneration and Neuroprotection in Parkinsons Disease. London: Academic Press, 1996: 209-218.

Creasy LL, Coffee M. Phytoalexin production potential of grape berries. J Am Soc Hort Sci 1988; 113(2):230-234.

Karuppagounder SS, Pinto JT, Xu H, Chen HL, Beal MF, Gibson GE. Dietary supplementation with resveratrol reduces plaque pathology in a transgenic model of Alzheimer's disease. Neurochemistry International 2009; 54 (2): 111-118.

Wood, JG, Rogina, B, Lavu S, Howitz, K, Helfand SL, Tatar, M, Sinclair, D. Sirtuin Activators mimic caloric restriction and delay ageing in metazoans. Nature. 2004; 430: 686-89.

Kim D, Nguyen MD, Dobbin MM, Fischer A, Sananbenesi F, Rodgers JT, Delalle I, Baur JA, Sui G, Armour SM, Puigserver P, Sinclair DA, Tsai LH. SIRT1 deacetylase protects against neurodegeneration in models for Alzheimer's disease and amyotrophic lateral sclerosis. EMBO J 2007; 26(13): 3169-79.

Anekonda TS. Resveratrol—a boon for treating Alzheimer's disease? Brain Research Reviews 2006; 52: 316-26.

Sharma M, Gupta YK. Chronic treatment with trans-resveratrol prevents intracerebroventricular streptozotocin induced cognitive impairment and oxidative stress in rats. Life Sciences 2002;71: 2489-98.

Kumar P, Padi SS, Naidu PS, Kumar A. Effect of resveratrol on 3-nitropropionic acid-induced biochemical and behavioural changes: possible neuroprotective mechanisms. Behavioural Pharmacology 2006; 17: 485-92.

Yang YB, Piao YJ. Effects of resveratrol on secondary damages after acute spinal cord injury in rats. Acta Pharmacologica Sinica 2003; 24: 703-10.

Sinha K, Chaudhary G, Gupta YK. Protective effect of resveratrol against oxidative stress in middle cerebral artery occlusion model of stroke in rats. Life Sciences 2002; 71: 655-65.

Yáñez, M, Fraiz, N, Cano, E, Orallo, F. Inhibitory effects of cis- and trans-resveratrol on noradrenaline and 5-hydroxytryptamine uptake and on monoamine oxidase activity. Biochem Biophys Res Commun 2006; 344: 688-95.

Li Y, Grupe A, Rowland C, Holmans P, Segurado R, Abraham R, Jones L, Catanese J, Ross D, Mayo K, Martinez M, Hollingworth P, Goate A, Cairns NJ, Racette BA, Perlmutter JS, O'Donovan MC, Morris JC, Brayne C, Rubinsztein DC, Lovestone S, Thal LJ, Owen MJ and Williams J. Evidence that common variation in NEDD9 is associated with to late-onset Alzheimer's and Parkinson's disease. Hum Mol Genet 2008; 17:759-767.

Walle T, Hsieh F, DeLegge MH, Oatis JE, Walle UK. High absorption but very low bioavailability of oral resveratrol in humans. Drug Metabolism and Disposition 2004; 32: 1377-82.

la Porte C, Voduc N, Zhang G, Seguin I, Tardiff D, Singhal N, Cameron DW. Steady-State Pharmacokinetics and Tolerability of Trans-Resveratrol 2000 mg Twice Daily with Food, Quercetin and Alcohol (Ethanol) in Healthy Human Subjects. Clinical Pharmacokinetics. 2010; 49: 449-454.

Boocock DJ, Faust GE, Patel KR, et al Phase I dose escalation pharmacokinetic study in healthy volunteers of resveratrol, a potential cancer chemopreventive agent. Cancer Epidemiology, Biomarkers & Prevention 2007; 16: 1246-52.

Marier JF, Vachon P, Gritsas A, Zhang J, Moreau JP, Ducharme MP. Metabolism and disposition of resveratrol in rats: extent of absorption, glucuronidation, and enterohepatic recirculation evidenced by a linked-rat model. The Journal of Pharmacology and Experimental Therapeutics 2002; 302 (1): 369-73.

Abd El-Mohsen M, Bayele H, Kuhnle G, et al. Distribution of [3H]trans-resveratrol in rat tissues following oral administration. The British Journal of Nutrition 2006; 96: 62-70.

Wenzel E, Soldo T, Erbersdobler H, Somoza V. Bioactivity and metabolism of trans-resveratrol orally administered to Wistar rats. Molecular Nutrition & Food Research 2005; 49: 482-94.

Yu C, Shin YG, Chow A, et al. Human, rat, and mouse metabolism of resveratrol. Pharmaceutical Research 2002; 19: 1907-14.

Wang LX, Heredia A, Song H, et al. Resveratrol glucuronides as the metabolites of resveratrol in humans: characterization, synthesis, and anti-HIV activity. Journal of Pharmaceutical Sciences 2004; 93: 2448-57.

Elliott PJ, Jirousek M. Sirtuins: novel targets for metabolic disease. Current Opinion in Investigational Drugs 2008; 9: 371-8.

Barber, EK, Chapter 4, CD33 is Phosphorylated in Myeloid Cell Lines. From: Barber EK: A Functional Analysis of CD33 and CD34, (Examined Thesis submitted to Oxford University Library, Jul. 1997).

Freeman SD, Kelm S, Barber, EK, and Crocker PR. Characterisation of CD33 as a new member of the sialoadhesin family of cell adhesion molecules. Blood 1995; 85:2005-2012.

Shults CW. Lewy bodies. Proc Natl Acad Sci U S A. 2006; 103: 1661-8.

Griffin JD, Linch D, Sabbath K, Larcom P, Schlossman SF: A monoclonal antibody reactive with normal and leukemic human myeloid progenitor cells. Leuk Res 1984; 8:521-34.

Uversky VN, Li J, Bower K, Fink AL. Synergistic effects of pesticides and metals on the fibrillation of alpha-synuclein: implications for Parkinson's disease. Neurotoxicology 2002; 23: 527-36.

Wood JG, Mirra SS, Pollock NJ, Binder LI. Neurofibrillary tangles of Alzheimer disease share antigenic determinants with the axonal microtubule -associated protein tau (r). Proc Natl Acad Aci U S A. 1986; 83:4040-3.

Kosik KS, Joachim CL, Selkoe DJ. Microtubule-associated protein tau® is a major antigenic component of paired helical filaments in Alzneimer disease. Proc Natl Acad Sci U S A 1986; 83: 4044-8.

Hutton M, Lendon CL, Rizzu P, Baker M, Froelich S, Houlden H, Pickering-Brown S, Chakraverty S, Issacs A, Grover A, et al. Association of missense and 5'-splice-site mutations in tau with the inherited dementia FTDP-17. Nature. 1998; 393:702-705.

Gotz J, Chen F, van Dorpe J, Nitsch RM. Formation of neurofibrillary tangles in P301I tau transgenic mice induced by Abeta 42 fibrils. Science. 2001; 293: 1491-5.

Lewis J, Dickson DW, Lin WL, Chisholm L, Corral A, Jones G, Yen SH, Sahara N, Skipper L, Yager D, Eckman C, Hardy J, Hutton M, McGowan E. Enhanced neurofibrillary degeneration in transgenic mice expressing mutant tau and APP. Science. 2001; 293:1487-91.

Reifert J, Hartung-Cranston D, Feinstein SC. Amyloid beta mediated cell death of cultured hippocampal cells. J Biol Chem 2011; 11:1-26.

Morishima-Kawashima M, Hasegawa M, Takio K, Suzuki M, Yoshida H, Watanabe A, Titani K, Ihara Y. Hyperphosphorylation of tau in PHF. Neurobiol Aging 1995; 16:365-380.

Lee G, Thangavel R, Sharma, VM, Litersky JM, Bhasker K, Fang, SM, Do LH, Andreadis, A, Van Hoesen G, and Ksiezak-Reding H. Phosphorylation of Tau by Fyn: Implications for Alzheimer's Disease. J Neurosci2004; 24:2304-2312.

Scales TME., Derkinderen P, Leung K-Y, Byers HL, Ward MA, Price C, Bird In, Perera T, Kellie S, Williamson R, Anderton BH, and Reynolds CH. Tyrosine Phosphorylation of Tau by the Src Family Kinases Lck and Fyn. Mol Neurodegen 2011; 6:12-36.

Lebouvier T, Scales TM, Hanger DP, Geahlen RL, Lardeux B, Reynolds CH, Anderton BH, Derkinderen P. The microtubule-associated protein tau is phosphorylated by Syk. Biochim Biophy Acta 2008; 1783:188-192.

(56) References Cited

OTHER PUBLICATIONS

Derkinderen P, Scales TM, Hanger DP, Leung KY, Byers HL, Ward MA, Lenz C, Price C, Bird IN, Perera T, Kellie S, Williamson R, Noble W, Van Etten RA, Leroy K, Brion JP, Reynolds CH, Anderton BH. Tyrosine 394 is phosphorylated in Alzheimer's paired helical filament tau and in fetal tau with c-Abl as the candidate tyrosine kinase. J Neurosci 2005; 25: 6584-6593.
He G, Luo W, Li P, Remmers C, Netzer WJ, Hendrick J, Bettayeb K, Flajolet M, Gorelick F, Wennogle LP, Greengard P. Gamma-secretase activating protein is a therapeutic target for Alzheimer's disease. Nature. 2010; 467:95-98.
Dai H, Marbach P, Lemaire M, Hayes M, Elmquist WF. Distribution of STI-571 to the brain is limited by P-glycoprotein-mediated efflux. J Pharmacol Exp Ther 2003; 304: 1085-92.
Hollingworth P, et. al., Common variants at ABCA7, MS4A6A/MS4A4E, EPHA1, CD33 and CD2AP are associated with Alzheimer's disease. Nat Genetics 2011; 43: 429-434.
Naj, AC. Common variants at MS4A4/MS4A6E, CD2AP, CD33 and EPHA1 are associated with late-onset Alzheimer's disease. Nat Genetics 2011; 43: 436-441.
Andrews RG, Torok-Storb B, Bernstein ID: Myeloid-associated differentiation antigens on stem cells and their progeny identified by monoclonal antibodies. Blood 62:124-132, 1983.
Taylor VC, Buckley CD, Douglas M, Cody AJ, Simmons DL, Freeman SD. The myeloid-specific sialic acid binding receptor, CD33, associates with the protein-tyrosine phosphatases, SHP-1 and SHP-2. J Biol Chem 1999; 274:11505-12.
Paul SP Taylor LS, Stansbury EK, and McVicar DW. Myeloid specific human CD33 is an inhibitory receptor with differential ITIM function in recruiting the phosphatases SHP-1 and SHP-2. Blood 2000; 96:483-490.
Wang J, Santa-Maria I, Ho L, Ksiezak-Reding H, Ono K, Teplow DB, Pasinetti GM. Grape derived polyphenols attenuate tau neuropathology in a mouse model of Alzheimer's disease. J Alzheimers Dis 2010; 22:653-61.
Wang Q, Xu J, Rottinghaus GE, Simonyi A, Lubahn D, Sun GY, Sun AY. Brain Res. Resveratrol protects against global cerebral ischemic injury in gerbils. 2002; 958: 439-47.
Donmez G, Wang D, Cohen DE, Guarente L. SIRT1 suppresses beta-amyloid production by activating the alpha-secretase gene ADAM10. Cell 2010; 142:320-332. Erratum in: Cell 2010; 142:494-5.
Ferreira ST, Vieira MN, De Felice FG. Soluble protein oligomers as emerging toxins in Alzheimer's and other amyloid diseases. IUBMB Life 2007; 59: 332-45.
Spillantini MG, Crowther RA, Jakes F, Hasegawa M, Goedert M. alpha-Synuclein in filamentous inclusions of Lewy bodies from Parkinson's disease and dementia with Lewy bodies. Proc Natl Acad Sci U S A. 1998; 95:6469-73.
Chen L and Feany MB. a-Synuclein phosphorylation controls neurotoxicity and inclusion formation in a Drosophila model of Parkinson disease. Nature Neuroscience 2005; 8: 657-663.
Chen L, Periquet M, Wang X, Negro A, McLean PJ, Hyman BT, Feany, MB. Tyrosine and serine phosphorylation of alpha-synuclein have opposing effects on neurotoxicity and soluble oligomer formation. J Clin Invest 2009; 119:3257-65.
Cavallarin N, Vicario M, Negro A. The role of phosphorylation in synucleinopathies: focus on Parkinson's disease. CNS Neurol Disord Drug Targets. 2010; 9:471-81.
Nakamura T, Yamashita H, Takahashi T and Nakamura S. Activated Fyn Phosphorylates a-Synuclein at Tyrosine Residue 125. Biochem and Biophys Res Comm 2001; 280:1085-1092.
Negro A, Brunati AM, Donella-Deana A, Massimino ML, Pinna LA. Multiple phosphorylation of alpha-synuclein by protein tyrosine kinase Syk prevents eosin induced aggregation. FASEB J 2002; 16:210-2.
Nakamura T, Yamashita H, Nagano Y, Takahashi T, Avraham S, Avraham H, Matsumoto M, Nakamura S. Activation of Pyk2/RAFTK induces tyrosine phosphorylation of a-synuclein via Src-family kinases. FEBS Letts. 2001; 521:190-194.

Montine TJ, Shi M, Quinn JF, Peskind ER, Craft S, Ginghina C, Chung KA, Kim H, Galasko DR, Jankovic J, Zabetian CP, Leverenz JB, Zhang J. CSF AP(42) and tau in Parkinson's disease with cognitive impairment. Mov Disord 2010; 25:2682-5.
Lei P, Ayton S, Finkelstein DI, Adlard PA, Masters CL, Bush AI. Tau protein: relevance to Parkinson's disease. Int J Biochem Cell Biol. 2010; 42:1775-8.
Williamson R, Scales T, Clark BR, Gibb G, Reynolds CH, Kellie S, Bird IN, Varndell IM, Shepppard PW, Everall I, Anderton BH. Rapid tyrosine phosphorylation of neuronal proteins includeing tau and focal adhesion kinase in response to amyloid-beta peptide exposure: involvement of Src family protein kinases. J Neurosci 2002; 22:10-20.
Vega IE, Cui L, Propst JA, Hutton ML, Lee G, Yen SH. Increase in tau tyrosine phosphorylation correlates with the formation of tau aggregates. Brain Res Mol Brain Res 2005; 138:135-144.
Kode A, Rajendrasozhan S, Caito S, Yang SR, Megson IL, Rahman I. Resveratrol induces glutathione synthesis by activation of Nrf2 and protects against cigarette smoke-mediated oxidative stress in human lung epithelial cells. American Journal of Physiology. Lung Cellular and Molecular Physiology 2008; 294: L478-88.
Fahn, S, Elton, R, Members of the UPDRS Development Committee. In: Fahn, S, Marsden, CD, Caine, DB, Goldstein, M, eds. Recent Developments in Parkinson's Disease, vol. 2. Florham Park, N. J. Macmillan Health Care Information 1987; pp. 153-163, 293-304.
Avery PJ, Jorgensen A, Hamberg AK, Wadelius M, Pirmohamed M, Kamali F. A proposal for an individualized pharmacogenetics-based warfarin initiation dose regimen for patients commencing anticoagulation therapy. Clin Pharmacol Ther 2011; 90:701-6.
Sun AY, Wang Q, Simonyi A and Sun GY. Resveratrol as a Therapeutic Agent for Neurodegenerative Diseases. Mol Neurobiol 2010; 41: 375-83.
Baur JA and Sinclair DA. Therapeutic potential of resveratrol: the in vitro evidence. Nat. Review Drug Discov. 2006; 5: 493-506.
Schults CW, Beal MF, Fontaine K, et al. Absorption, tolerability and effects on mitochondrial activity of oral coenzyme Q10 in parkinsonian patients. Neurology 1998; 50: 793-795.
Tanaka M, Sotomatsu A, Kanal H, et al. Dopa and dopamine cause cultured neuronal death in the presence of iron. J Neuronal Sci. 1991; 101: 198-203.
Agid Y, Ahlskog E, Albanese A, et al. Levodopa in the treatment of Parkinson's disease. Mov. Disord. 1999; 14: 911-913.
Parkkinen L, O'Sullivan SS, Kuoppamäki M, et al. Does levodopa accelerate the pathologic process in Parkinson disease brain? Neurology 2011;77;1420-1426.
LeWitt, Peter A. MD; Dubow, Jordan MD; Singer, Carlos MD. Is levodopa toxic?: Insights from a brain bank. Neurology 2011; 77: 1414-1415.
Pahan K, Sheikh GS, Nmboodri AMS, et al. N-acetyl cysteine inhibits induction of NO production by endotoxin or cytokine stimulated rat peritoneal macrophages, C6 glial cells and astrocytes. Free Rad Biol and Med 1998; 24: 39-48.
Crook TH, Tinkelenberg J, Yesavage J. Effects of phosphatidylserine in age-associated memory impairment. Neurology 1991; 41: 644-49.
Steffen V, Santiago M, de la Cruz CP, et al. Effect of intraventricular injection of 1-methyl-4-phenylpridinium protection by acetyl-L-carnitine. Human Exp Toxicol 1995; 14: 865-871.
Thal L J, Carta A, Clarke WR, et al. A 1-year multicenter placebo-controlled study of acetyl-L-carnitine in patients with Alzheimer's disease. Neurology 1996; 47: 705-711.
Marangon K, Deveraj S, Tirosh O, et al. Comparison of the effect of a-lipoic acid and a-tocopherol supplementation on measures of oxidative stress. Free Rad Biol and Med 1999; 27: 1114-1121.
Shults CW, Oakes D, Kieburtz K, Beal MF, Haas R, Plumb S, Juncos JL, Nutt J, Shoulson I, Carter J, Kompoliti K, Perlmutter JS, Reich S, Stern M, Watts RL, Kurlan R, Molho E, Harrison M, Lew M. Effects of coenzyme Q10 in early Parkinson disease: evidence of slowing of the functional decline. Parkinson Study Group. Arch Neurol 2002; 59:1541-50.

(56) References Cited

OTHER PUBLICATIONS

Le Bars P, Katz MM, Berman N, et al. A Placebo-Controlled, Double-blind Randomized Trial of an Extract of Gingko Biloba for Dementia, JAMA 1997; 278: 1327-32.

Kwon KJ, Kim HJ, Shin CY, Han SH. Melatonin Potentiates the Neuroprotective Properties of Resveratrol Against Beta-Amyloid-Induced Neurodegeneration by Modulating AMP-Activated Protein Kinase Pathways. J Clin Neurol 2010; 6:127-37.

Block G, Liss C, Reines S, et al. Comparison of immediate release and controlled release carbidopa/levodopa in Parkinson's Disease. A multicenter 5-year study. The CR First Study Group. Eur Neurol 1997; 37: 23-27.

Koller WC, Hutton JT, Tolosa E, et al. Immediate-release and controlled release carbidopa/levodopa in PD: a 5-year randomized multicenter study. Neurology 1999; 53: 1012-1019.

Xu Y, Wang Z, You W, Zhang X, Li S, Barish PA, Vernon MM, Du X, Li G, Pan J, Ogle WO. Antidepressant-like effect of trans-resveratrol: Involvement of serotonin and noradrenaline system. Eur Neuropsychopharmacol 2010; 20:405-13.

Hauser RA. Early pharmacologic treatment in Parkinson's disease. Am J Manag Care 2010; 16: S 100-7.

Shulman, LM, Gruber-Baldini, AL, Anderson, KE, Fishman, PS, Reich, SG, and Weiner, WW. The Clinically Important Difference on the Unified Parkinson's Disease Rating Scale. Arch Neurol 2010; 67: 64-70.

Hauser RZ, Lyons KE, Pahwa R, Zesiewica TA, Golbe LI., In: Chapter 5: Medications for the Treatment of Parkinson's Disease. From: Parkinson's Disease: Questions and Answers, 4th ed. West Palm Beach: Merit Publishing International; 2003: pp. 79-85.

Goetz CG, Koller WC, Poewe W, Rascol O, Sampaio C. Management of Parkinson's Disease: An evidence-based review. Mov Disord 2002; 17(suppl 4): S1-S166.

Goetz CG, Poewe W, Rascol O, Sampaio C. Evidence-based medical review update: Pharmacological and surgical treatments of Parkinson's disease: 2001-2004. Mov Disord 2005; 20: 523-539.

Moretto A and Colosio C. Biochemical and toxicological evidence of neurological effects of pesticides: the example of Parkinson's disease. Neurotoxicology 2011; 32: 383-91.

Chiang PK, Lam MA, Luo Y. The many faces of amyloid beta in Alzheimer's disease. Curr Mol Med 2008; 8: 580-4.

Clinical study to Assess the Effects of SRT2104 and Prednisolone on Biomarker Volunteers; ClinicalTrials.gov, ClinicalTrials.gov Identifier: NCT00920660, Jun. 12, 2009.

Effect of SRT2379 on Endotoxin-Induced Inflammation; ClinicalTrials.gov, Clinical Trials.gov Identifier NCT01262911, Dec. 16, 2010.

"SINEMET® (carbidopa-levodopa) Tablets" package insert, Merck & Co., Inc. (1996 revised 2013), pp. 1-9.

"SINEMET® CR (carbidopa-levodopa) Sustained-ReleaseTablets" package insert, Merck & Co., Inc. and Bristol-Myers Squibb Company (1996, revised 2009), pp. 1-19.

* cited by examiner

TREATMENT OF NEURODEGENERATIVE DISEASE

CROSS REFERENCE TO RELATED APPLICATION

This application is a continuation-in-part of International Application No. PCT/US11/57544, filed Oct. 24, 2011, which claims the benefit of U.S. Provisional Application No. 61/405,987, filed Oct. 22, 2010, U.S. Provisional Application Ser. No. 61/470,519, filed Apr. 1, 2011, and U.S. Provisional Application 61/470,608, filed Apr. 1, 2011, each of which is incorporated by reference herein in its entirety.

BACKGROUND OF THE INVENTION

1. Field of the Invention

The invention is related to a method of treating a neurodegenerative disease, such as, for example, Parkinson's Disease.

2. Description of Related Art

Parkinson's Disease is a progressive neurodegenerative disorder characterized by any combination of slowness of movement (bradykinesia), tremors, exaggerated movements from excess dopamine (dyskinesia), muscle-stiffness, freezing in place while attempting to walk (akinesia), and a progressive loss of cognition. Current treatment standard for Parkinson's Disease is SINEMET® 25/100, a carbidopa (25 mg)/levodopa (100 mg) tablet (Merck & Co.), available in standard (STD) and controlled-release (CR) forms. Although SINEMET® helps improve movement, it does little to aid the decline in cognition; thus other treatments are needed to slow both the decline in movement and cognition.

Carbidopa reduces the amount of levodopa required to produce a given response by about 75% and, when administered with levodopa, increases both plasma levels and the plasma half-life of levodopa, and decreases plasma and urinary dopamine and homovanillic acid. The plasma half-life of levodopa is about 50 minutes, without carbidopa. When carbidopa and levodopa are administered together, the half-life of levodopa is increased to about 1.5 hours. At steady state, the bioavailability of carbidopa from SINEMET® tablets is approximately 99% relative to the concomitant administration of carbidopa and levodopa.

SINEMET® is an immediate-release formulation of carbidopa-levodopa that is designed to begin release of ingredients within 30 minutes; thus the drug should be taken at regular intervals according to the schedule outlined by the physician.

One of the side effects reported with SINEMET® is a sudden onset of sleep during daily activities, in some cases without awareness or warning signs, when they are taking dopaminergic agents, including levodopa. Thus, patients should be advised to exercise caution while driving or operating machinery and that if they have experienced somnolence and/or sudden sleep onset, they must refrain from these activities. Further, there have been reports of patients experiencing intense urges to gamble, increased sexual urges, and other intense urges, including hoarding, and the inability to control these urges while taking one or more of the medications that increase central dopaminergic tone and that are generally used for the treatment of Parkinson's Disease, including SINEMET®.

Co-administration of SINEMET® with other drugs could also lead to undesirable side-effects. For example, symptomatic postural hypotension occurred when SINEMET® was added to the treatment of a patient receiving antihypertensive drugs. Therefore, SINEMET® therapy may require dosage adjustment of the antihypertensive drug. Importantly, nonselective monoamine oxidase (MAO) inhibitors (Type A or B) are contraindicated for use with SINEMET®. The SINEMET® package insert states that these inhibitors should be discontinued at least two weeks prior to initiating therapy with SINEMET®. SINEMET®, however, may be administered concomitantly with the manufacturer's recommended dose of an MAO inhibitor with selectivity for MAO type B (e.g., selegiline hydrochloride).

Other currently available options for treating patients with Parkinson's Disease include monoamine oxidase B (MAO-B) inhibitors rasagiline (AZILECTt®) and selegiline (EL-DEPRYL®). Rasagiline and selegiline, alone or in combination with other medications, are frequently the first course of Parkinson's Disease therapy prior to starting SINEMET® because they have been shown to delay the appearance of SINEMET® (levodopa)-induced dyskinesias (The Parkinson Study Group, *Arch. Neurol.* 2002; Parkinson Study Group, *Arch. Neurol.*, 1989).

Selegiline, but not rasagiline, was shown to provide neuroprotective effects based on its ability to delay the emergence of disability and the progression of motor symptoms in comparison with a placebo (Parkinson Study Group, *N. Engl. J. Med.,* 1989). Selegiline neuroprotection is believed to result from the upregulation of antioxidant and anti-apoptotic molecules such as glutathione, superoxide dismutase (SOD), and BCL-2 (Mytilineou, et al., *J. Pharmacol. Exp. Ther.,* 1998; Tatton, et al., *J. Neurochem.,* 1994; Tatton, et al., *Neurodegeneration and Neuroprotection in Parkinson's Disease,* 1996). However, concomitant therapy with selegiline and carbidopa-levodopa may be associated with severe orthostatic hypotension not attributable to carbidopa-levodopa alone. As the dose of selegiline is increased, its selectivity to inhibit only MAO-B decreases and MAO-A inhibition may also occur. (Hauser, et al., 2003); Goetz, et al., *Mov. Disord.,* 2002; Goetz, et al. *Mov. Disord.,* 2005)

Resveratrol is a common name for 3,5,4'-trihydroxystilbene, which exists as two geometric isomers: cis- (Z) and trans- (E). Resveratrol is found to be most concentrated in the skins of red grapes (Creasey, et al., J Am Soc Hortic Sci, 1988) and has been shown to decrease plaque formation in Alzheimer's mouse brain (Karruppagounder, et al., *Neurochemistry International,* 2009), to activate the Sir 2 sirtuin gene (whose homolog in mammals is known as SIRT1), which promotes longevity (Wood, et al., Nature, 2004), and to be neuroprotective in neurodegeneration models in Alzheimer's Disease and Amyotrophic Lateral Sclerosis, (Kim, et al., EMBO J., 2007), as well as other studies, (Anekonda, et al., Brain Research Reviews, 2006; Sharma, et al., Life Sciences, 2002; Kumar, et al., Behavioral Pharmacology, 2006; Yang, et al., Acta Pharmacologica Sinica, 2003; Sinha, et al., Life Sciences, 2002). The recent finding that Alzheimer's disease and Parkinson's Disease genes reside on a common locus is a further indication that resveratrol is likely to be of benefit to both diseases (Li, et al., Hum. Mol. Genet., 2008).

In studies of rat brain, trans-resveratrol, 3,5,4'-trihydroxy-trans-stilbene (t-RES) was shown to inhibit monoamine oxidase A (MAO-A) slightly more than MAO-B, with t-RES inhibiting both MAOs more than cis-resveratrol (c-RES) indicating that resveratrol has a similar chemical structure to some antidepressants (Yáñez, et al., Biochem. Biophys. Res. Commun., 2006).

Although, about 70% of the resveratrol dose given orally as a pill is absorbed, oral bioavailability of resveratrol is low because it is rapidly metabolized in intestines and liver into conjugated forms: glucuronate and sulfonate (Walle, et al., *Drug Metabolism and Disposition*, 2004). Only trace amounts (below 5 ng/mL) of unchanged resveratrol could be detected in the blood after 25 mg oral dose (LaPorte, et al., *Clinical Pharmacokinetics*, 2010).

Full formal pharmacokinetics of oral resveratrol 2000 mg taken twice daily in humans, studying the interaction with concurrent ethanol, quercetin and a fatty meal has been reported (LaPorte, et al., *Clinical Pharmacokinetics*, 2010). Mean peak serum resveratrol concentration was 1274 ng/mL at steady-state, which was reduced 46% by a fatty meal at dosing. There was no effect of concurrent oral quercetin or ethanol. Healthy volunteers given resveratrol had frequently reported minor diarrhea, and laboratory measures identified slight changes in liver function tests and serum potassium. No adverse effect on renal function was identified, although only eight healthy adults were observed in the two-week study. A small study showed no adverse effects of up to 5 g of resveratrol in healthy volunteers (Boocock, et al, *Cancer Epidemiology, Biomarkers & Prevention*, 2007).

Less than 5% of the oral dose is being observed as free resveratrol in blood plasma in humans (Boocock, et al., *Cancer Epidemiology, Biomarkers & Prevention*, 2007; Walle, et al., *Drug Metabolism and Disposition*, 2004) and rats (Marier, et al., *The Journal of Pharmacology and Experimental Therapeutics*, 2002; Abd El-Mohsen, et al., *The British Journal of Nutrition*, 2006; Wenzel, et al., *Molecular Nutrition & Food Research*, 2005.) The most abundant resveratrol metabolites in humans, rats, and mice are trans-resveratrol-3-O-glucuronide and trans-resveratrol-3-sulfate (Yu, et al., *Pharmaceutical Research*, 2002). Walle et al. suggests sulfate conjugates are the primary source of activity (*Drug Metabolism and Disposition*, 2004), Wang et al. suggests the glucuronides, Wang, et al., *Journal of Pharmaceutical Sciences*, 2004) and Boocock et al. also emphasized the need for further study of the effects of the metabolites, including the possibility of deconjugation to free resveratrol inside cells.

A formulation of resveratrol in a chewing gum form is now in production, and this would be expected to achieve much higher blood levels than oral formulations. Resveratrol given in a proprietary formulation SRT501 (3 or 5 g), developed by Sirtris Pharmaceuticals, reached five to eight times higher blood levels. These levels did approach the concentration necessary to exert the effects shown in animal models and in vitro experiments (Elliott, et al., *Current Opinion in Investigational Drugs*, 2008). However, clinical trials were terminated due to kidney failure in some patients in December 2010 [ClinicalTrials.gov Identifier: NCT00920556].

Other more bioavailable SIRT1 activators, SRT2104 and SRT2379 are currently being tested in exploratory clinical trials (ClinicalTrials.gov Identifiers: [NCT00920660] and [NCT01262911]

In contrast, no studies have been carried out to date evaluating effectiveness and tolerability of the "less bioavailable" or naturally occurring form of t-RES in ameliorating the symptoms of Parkinson's Disease even at relatively high concentrations.

Accordingly, the inventor has identified a need in the art to provide a method for testing a therapeutic benefit such as, for example, improving the pharmacokinetics of SINEMET® making it more potent and longer-lasting, and potential anticoagulant risks of t-RES supplements in patients with Parkinson's Disease, a method for treating a neurodegenerative disease, and a method for reducing alpha-synuclein amyloid proteins in a patient suffering from Parkinson's Disease.

SUMMARY OF THE INVENTION

It is against the above background that the present invention provides certain unobvious advantages and advancements over the prior art.

Although the present invention is not limited to specific advantages or functionality, it is noted that the present invention provides a method for reducing alpha-synuclein amyloid proteins in a patient suffering from Parkinson's Disease comprising administering to the patient an effective amount of resveratrol.

The present invention further provides a method of treating a neurodegenerative disease associated with amyloid proteins comprising administering to a patient in need thereof an effective amount of resveratrol.

The present invention yet further provides a method for treating Parkinson's Disease comprising administering to a patient in need thereof a pharmaceutically effective amount of carbidopa, levodopa, and resveratrol.

In one particular aspect, the method of the invention may include administering glutathione to the patient. In another particular aspect, the method of the invention may include administering to the patient one or more of magnesium citrate, N-acetyl-L-cysteine, phosphatidylserine, acetyl-L-carnitine, alpha lipoic acid and Coenzyme Q10.

In one particular embodiment the present invention provides a method of reducing the pharmaceutically effective dose of at least one of carbidopa and levodopa in the treatment of Parkinson's Disease comprising administering to a patient receiving at least one of carbidopa and levodopa an effective amount of resveratrol.

In yet another particular embodiment the present invention provides a method of improving cognition, speech and/or movement in a patient suffering from Parkinson's Disease comprising administering to the patient carbidopa, levodopa and resveratrol.

In one particular aspect, the method may include administering to the patient one or more of glutathione, magnesium citrate, N-acetyl-L-cysteine, phosphatidylserine, acetyl-L-carnitine, alpha lipoic acid and Coenzyme Q10.

In yet another aspect, the invention is directed to a method of regulating and/or reducing dyskinesia in a patient suffering from Parkinson's Disease that includes administering to the patient an effective amount of resveratrol, carbidopa and levodopa.

In any or all embodiments of the invention, the resveratrol may be trans-resveratrol.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE FIGURES

The following detailed description of the embodiments of the present invention can be best understood when read in conjunction with the following drawings, where like structure is indicated with like reference numerals and in which.

Trans-resveratrol appears to enhance SINEMET®'s action, thus requiring less SINEMET® per dose.

DETAILED DESCRIPTION

Before describing the present invention in detail, a number of terms will be defined. As used herein, the singular forms "a", "an", and "the" include plural referents unless the context clearly dictates otherwise.

The following are provided for exemplification purposes only and are not intended to limit the scope of the invention described in broad terms above. All references cited in this disclosure are incorporated herein by reference.

The clinical features which define Parkinson's Disease are resting tremor, often beginning in one finger, bradykinesia (slowness of movement) and rigidity. In contrast to Alzheimer's Disease, cognitive ability usually remains intact in Parkinson's Disease until the latter stages of the disease (Irvine, et al., *Mol. Med.*, 2008). Pathologically, the pars compacta portion of the substantia nigra is the most obviously affected brain structure, which can only be confirmed post mortem by a histopathological examination of the substantia nigra for loss of pigmented neurons and presence of Lewy bodies in remaining neurons. Lewy bodies are predominantly comprised of alpha-synuclein (Shults, C. W., *Proc. Natl. Acad. Sci.*, 2006), which forms the core, surrounded by ubiquitin, as shown with immunostaining and examination by electron microscopy (Spillantini, et al., *Proc. Natl. Acad. Sci.*, 1998). A number of studies have shown that the oligomerization of alpha-synuclein is responsible for initiating the symptoms of Parkinson's Disease (Irvine, et al., *Mol. Med.* 2008). Among these studies, alpha-synuclein aggregation is shown to increase in the presence of metals and pesticides, which have been reported to be environmental risk factors for Parkinson's Disease (Moretto A and Colosio C., *Neurotoxicology.* 2011; Uversky, et al., *Neurotoxicology,* 2002). These studies, taken together with the finding that trans-resveratrol (t-RES) has been shown to reduce the formation of amyloid plaques in mouse brain, strongly suggest that the mechanism by which t-RES is improving symptoms in a Parkinson's Disease patient is by acting to reduce the levels of alpha-synuclein amyloid proteins in the brain. Aggregated amyloid-beta protein has also been found to be toxic in Alzheimer's Disease.

Twenty diseases have been discovered thus far in which amyloid proteins are found to be toxic as shown in Table 1 (See The International Society of Amyloidosis classifies amyloid fibrils based upon associated proteins; Sipe J D, et al. "Amyloid fibril protein nomenclature: 2010 recommendations from the nomenclature committee of the International Society of Amyloidosis". *Amyloid,* 2010).

TABLE 1

Diseases carrying toxic amyloid proteins

| Disease | Protein featured | Official Abbreviation | References |
|---|---|---|---|
| Alzheimer's Disease | Beta amyloid | Aβ | See, Chiang, et al., *Current Molecular Medicine,* 2008; Irvine, et al., *Molecular Medicine,* 2008; Ferriera, et al., *IUBMB Life,* 2007.; |
| Diabetes mellitus type 2 | IAPP (Amylin) | AIAPP | See, Haataja, et al., *Endocrine Reviews,* 2008; Höppener, *NEMJ,* 2000.; |
| Parkinson's disease | Alpha-synuclein | None | Irvine, et al., *Molecular Medicine,* 2008. |
| Transmissible spongiform encephalopathy, e.g. Bovine spongiform encephalopathy | Prion | APrP | More than Just Mad Cow Disease, *Nature Structural Biology,* 2001. |
| Huntington's Disease | Huntingtin | None | Truant, et al., *The FEBS Journal,* 2008; Weydt, *Expert Op. on Ther. Targets,* 2006. |
| Medullary carcinoma of the thyroid | Calcitonin | ACal | Baethge and Jacobsen, *Amyloidosis Overview.* |
| Cardiac arrhythmias, Isolated atrial amyloidosis | Atrial natriuretic factor | AANF | |
| Atherosclerosis | Apolipoprotein AI | AApoA1 | |
| Rheumatoid arthritis | Serum amyloid A | AA | |
| Aortic medial amyloid | Medin | AMed | |
| Prolactinomas | Prolactin | APro | |
| Familial amyloid polyneuropathy | Transthyretin | ATTR | |

TABLE 1-continued

Diseases carrying toxic amyloid proteins

| Disease | Protein featured | Official Abbreviation | References |
|---|---|---|---|
| Hereditary non-neuropathic systemic amyloidosis | Lysozyme | ALys | |
| Dialysis related amyloidosis | Beta 2 microglobulin | Aβ2M | |
| Finnish amyloidosis | Gelsolin | AGel | |
| Lattice corneal dystrophy | Keratoepithelin | Aker | |
| Cerebral amyloid angiopathy | Beta amyloid | Aβ | Dotti, et al., *Nat. Cell Biol.*, 2009. |
| Cerebral amyloid angiopathy (Icelandic type) | Cystatin | ACys | |
| Systemic AL amyloidosis | Immunoglobulin light chain A | AL | Baethge and Jacobsen, *Amyloidosis Overview*. |
| Sporadic Inclusion Body Myositis | S-IBM | none | |

That amyloid proteins are implicated in many different diseases and that t-RES has been shown to reduce the number of amyloid plaques in mice with Alzheimer's Disease, strongly suggests that t-RES may provide a treatment for any or all of the affected diseases, in addition to Alzheimer's Disease and Parkinson's Disease.

Thus, priority in the amyloids to be tested in Parkinson's Disease animal models would be given to alpha-synuclein proteins as they have been identified on autopsy in the brains of previously diagnosed Parkinson's Disease patients and are likely responsible for the symptoms of Parkinson's Disease. If possible, Alzheimer's Disease mice expressing amyloid-beta and tau proteins, treated with t-RES, would be used for comparison. The success of t-RES in treating Alzheimer's Disease and now a Parkinson's Disease patient strongly suggest that it should be tested on the amyloid proteins implicated in the remaining diseases above in rodent models and patients to look for ameliorating effects in those diseases as well. Prevention of phosphorylation or de-phosphorylation is the likely mechanism through which t-RES is acting to reduce and/or reverse neurodegeneration.

The hallmarks of Alzheimer's Disease pathology are amyloid-β aggregates or plaques and neurofibrillary tangles. In Alzheimer's Disease, neurofibrillary tangles containing the hyperphosphorylated microtubule-associated tau protein have been shown be neurotoxic (Wood, et al., *Proc. Natl. Acad. Aci*, 1986; Kosik, et al., *Proc. Natl. Acad. Sci*, 1986). Neurofibrillary tangles are also found in the 'tauopathies' which include frontotemporal dementia with Parkinsonism linked to chromosome 17 (FTDP-17), Pick's disease, progressive supranuclear palsy and corticobasal degeneration. The presence of tau deposits in this neurodegenerative disease, particularly FTDP-17, the patients of which have mutations in the tau gene itself (Hutton, et al., Nature, 1998) suggests that the tau protein may have an important role in the neurodegenerative process.

Tau hyperphosphorylation likely occurs downstream of the abnormal aggregation of amyloid-β plaques, producing Alzheimer's Disease symptoms (Gotz, et al., *Science*, 2001; Lewis, et al., *Science*, 2001). Recent evidence, however, suggests that amyloid-β plaque formation does not produce tau hyperphosphorylation, but only tau fragments which are then phosphorylated (Reifert, et al., *J. Biol. Chem.*, 2011). Tau is principally hyperphosphorylated by serine and threonine kinases (Morishima-Kawashima, et al., *Neurobiol Aging*, 1995) in addition to the non-receptor tyrosine kinases fyn on Tyr18 (Lee, et al., *J. Neurosci.*, 2004) and Tyr197 (Scales, et al., *Mol. Neurodegen*, 2011), syk on Tyr18 (Lebouvier, et al., *Biochim Biophy Acta.*, 2008), c-abl on Tyr394 (Derkinderen, et al., *J. Neurosci.*, 2005) and lck on Tyr18, Tyr197, Tyr310, Tyr394 and probably Tyr29 (Scales, et al., *Mol. Neurodegen.*, 2011). The finding that c-abl phosphorylated tyrosine in tau suggested the highly successful c-abl phosphotyrosine kinase inhibitor imatinib (GLEEVEC®) as therapy for Alzheimer's Disease by attaching itself to the gamma secretase activating protein (GSAP or protein pigeon homolog) (He, et al., *Nature*, 2010) however, imatinib is not able to cross the blood-brain barrier in mice (Dai, et al., *J. Pharmacol. Exp. Ther.*, 2003).

Through the Alzheimer Disease Genetics Consortium (ADGC) CD33 has recently been found to be a common variant associated with both AD (Hollingworth, *Nat. Genetics*, 2011) and late-onset Alzheimer's Disease (Naj, A C., *Nat. Genetics*, 2011). CD33 is a member of the immunoglobulin superfamily (Andrews, et al., *Blood*, 1983) and was originally identified as an important differentiation marker to distinguish between Acute and Chronic Myelogenous Leukemia (Griffin, et al., *Leuk Res.* 1984). Subsequently, it was shown to bind to sialic acid and share structural features with other sialic acid binding proteins, giving rise to the "sialic-acid binding immunoglobulin-related lectin" or siglec family (Freeman, et al., *Blood*, 1995). CD33 has two immunoreceptor tyrosine inhibitory motif (ITIM) tyrosine kinase domains, one of which may be an ITAM, and associates with the src-related non-receptor protein tyrosine kinases fgr, fyn, hck and lyn (Barber, E. K., Examined thesis submitted to Oxford Univ., 1997). Subsequently, CD33 was also shown to associate with tyrosine phosphatases (Taylor, et al., *J. Biol. Chem.*, 1999) suggesting that it may act as a regulatory receptor for phosphorylation, confirmed by a subsequent study (Paul, et al., *Blood*, 2000).

Polyphenols, such as t-RES, have recently been shown to decrease the phosphorylation of tau, thus inhibiting its toxicity (Wang, et al., *J. Alzheimers Dis.*, 2010). Thus, it is proposed that the mechanism by which t-RES reduces amyloid plaque formation in the mouse brain is by inhibiting the phosphorylation of tau and possibly CD33. It is thus proposed that a therapeutic strategy employing both t-RES and a phosphotyrosine kinase inhibitor directed at CD33 would be reasonable to pursue. Previous studies in Alzheimer's Disease argue for (Wang, et al, *Brain Res.*, 2002), and against (Donmez, et al., *Cell*, 2010) t-RES crossing the blood-brain barrier. The current studies on resveratrol on mice with Alzheimer's Disease (Karuppagounder, et al., *Neurochem Int.*, 2009) and the present study on a Parkinson's patient confirm the finding that t-RES can indeed cross the blood-brain barrier giving it an enormous therapeutic advantage.

In Parkinson's Disease, phosphorylated alpha-synuclein is found to be toxic to dopaminergic neurons in the substantia nigra (Spillantini, et al., *Proc. Natl. Acad. Sci.*, 1998). In contrast to tau, the tyrosine phosphorylation of alpha-synuclein in a drosophila model was shown to reduce toxicity while its serine phosphorylation at ser129 by casein kinase 1 (CK-1) or G-protein receptor kinase (GPRK) (Chen, et al., *Nature Neuroscience*, 2005) promoted toxicity (Chen, et al., *J. Clin. Invest.*, 2009). A neuroprotective effect of phosphorylation at ser87/tyr125 has been suggested (Cavallarin, et al., *CNS Neurol. Disord. Drug Targets*, 2010). Alpha-synuclein is tyrosine phosphorylated at tyr125 by fyn (Nakamura, et al., *Biochem and Biophys Res. Comm.* 2001), lyn, fgr, and syk, which also phosphorylates Tyr133 and Tyr136 and prevents protein aggregation (Negro, et al., *FASEB J.*, 2002). The src tyrosine kinases are activated by the protein tyrosine kinase Pyk2/RAFTK (Nakamura, et al., *FEBS Letts.*, 2001). Thus, based on the finding that polyphenols reduce phosphorylation, and thus toxicity in tau, it is reasonable to propose that the mechanism by which t-RES has been shown to improve Parkinson's Disease symptoms is via reducing the serine phosphorylation of alpha-synuclein. The observation that giving an increased dose of t-RES improves symptoms when improvement plateaus suggests that there may be a competitive interaction between increasing toxic phosphorylation of alpha-synuclein/tau and the ameliorating reduction of phosphorylation by t-RES.

A reasonable therapeutic strategy may thus be to augment t-RES treatment with a phosphotyrosine kinase agonist. About 10-30% of patients with Parkinson's Disease demonstrate Alzheimer's Disease-like symptoms as Parkinson's Disease progresses and those with Parkinson's Disease Dementia (PDD) have been shown to have amyloid-β plaques (Scales, et al., *Mol. Neurodegen.*, 2011) and abnormally increased cerebrospinal fluid (CSF) serine/threonine phosphorylated P181-tau (Montine, et al., *Mov. Disord.*, 2010). Other work suggests that among the six different isoforms of tau, there is suggestive experimental evidence that alpha-synuclein may play a role in tau phosphorylation (Lei, et al., *Int. J. Biochem. Cell Biol.*, 2010). These findings suggest that t-RES would help ameliorate the symptoms of both groups of patients, while therapies targeting tyrosine kinases would have to be addressed individually. If CD33 is also associated with Parkinson's Disease, a specific tyrosine-kinase enhancer may be appropriate. t-RES alone would be the safest strategy, however.

It is known that tyrosine phosphorylation of tau increases in fetal brain development, decreases in the normal adult brain, and increases in the brain affected with Alzheimer's Disease (Williamson, et al., *J. Neurosci.*, 2002; Derkinderen, et al., *J. Neurosci.*, 2005; Vega, et al., *Brain Res. Mol*, 2005). Inversely, phosphatases are known to be reduced in fetal development, to increase in the adult brain, followed by a decrease in the elderly, particularly upon neurodegeneration. These findings correlate well with the increased phosphorylation seen in the relevant Alzheimer's Disease and Parkinson's Disease sites. Interestingly, the finding that polyphenols dephosphorylate tau suggest that they act as phosphatases to dephosphorylate tau while activating SIRT1 which likely explains the apparent reversal of neurological damage observed in the patient with Parkinson's Disease in this study.

t-RES is suspected to reduce the level of toxic amyloid proteins in Parkinson's Disease including oligomerized alpha-synuclein. Dietary supplementation with t-RES has been shown to reduce the number of amyloid plaques in mouse brain in a transgenic model of Alzheimer's Disease (Karuppagounder, et al., *Neurochemistry International*, 2009). As described above, t-RES has been shown to activate SIRT1, and improve symptoms in patients suffering from Alzheimer's Disease, Multiple Sclerosis (MS), and various cancers. The common genetic linkage discovered between Alzheimer's Disease and Parkinson's Disease suggests that t-RES could reduce PD symptoms as well.

The inventor has demonstrated an unexpectedly beneficial effect of t-RES on a patient with Parkinson's Disease undergoing treatment with SINEMET® and/or CR and/or liquid glutathione. Importantly, the effect of a reduction in glutathione was observed in accordance with previous data suggesting a glutathione/resveratrol interaction. Although, as mentioned above, both selegiline and rasagiline are approved as therapy in conjunction with SINEMET®, neither was tolerated by the patient with Parkinson's Disease in this study.

Specifically, the inventor has demonstrated that a standard dose of t-RES given each morning to a 75-year old female stage-four Parkinson's Disease patient exhibiting a marked decline in speech and cognition, no dyskinesias, and progressive weakness, improved overall functioning and necessitated a reduction in the previously prescribed dosage of SINEMET® and SINEMET® CR.

Further, the inventor has demonstrated that upon treatment with t-RES, as described in details below, the patient unexpectedly showed a marked improvement in cognition and movement the next day followed by the elimination of nearly all hallucinations. Yet further, although an apparent a plateau in improvement appeared after about two months of treatment, the patient's cognition has stabilized as evidenced also by increased dyskinesias from SINEMET®, a reduced need for SINEMET®, going from 1½ tablets per day (150 mg levodopa) to one tablet per day (100 mg levodopa) in the first few days of t-RES administration.

Importantly, SINEMET® could not be taken at all by the patient at 7 am due to pronounced dyskinesias, and after about two months only ¼ pill could be given at 7 am, which still produced dyskinesias. Due to pronounced dyskinesias, which were severe enough to produce neck strain, after the administration of the resveratrol, SINEMET® was only given as ¼ pill when tremors were present. SINEMET® was not given in the presence of severe dyskinesias but was necessary with minor dyskinesias to prevent the occurrence of an "off" period which could lead to "freezing".

The patient had previously been taking READISORB® (liposomal glutathione drink), BRAIN SUSTAIN® (a nutritional supplement containing magnesium citrate, N-acetyl-L-cysteine, phosphatidylserine, acetyl-L-carnitine, alpha lipoic acid and Coenzyme Q10), the prescribed dose of SINEMET® STD and CR, and Aricept® (donepezil hydrochloride; Pfizer) among other drugs when the resveratrol was first administered. The patient was also undergoing a warm-pool physical therapy regime twice weekly for at least one year prior to and during this study. When the glutathione was removed from the treatment protocol, the patient's condition worsened, consistent with a previous study which demonstrated the decrease of available glutathione in murine brain upon the administration of resveratrol (Karuppagounder, et al., *Neurochemistry International*, 2009). In contrast, resveratrol was previously shown to protectively increase glutathione in response to cigarette smoke (Kode, et al., *American Journal of Physiology*, 2008). Thus, glutathione appears to enhance the benefits of t-RES.

As described in detail below, the parameters used to measure these findings were basic observations of speech, gait, overall function and tremor before and after administering t-RES over a period of months using the author's Tremor Rating Scale (TRS) in addition to the UPDRS (Fahn, et al., *Recent Developments in Parkinson's Disease*, 1989). Furthermore, the anticoagulant effects of t-RES were measured with a standard International Normalized Ratio (INR; a measure of clotting speed in the blood) anticoagulation test and shown to be negligible, as the patient's blood coagulation levels remained within the normal range. The International Normalized Ratio is a measure of clotting speed in the blood used especially as an indicator of Warfarin levels in the blood in patients with Atrial Fibrillation who need reduced clotting probability, to prevent strokes and pulmonary embolisms—but not so reduced as to increase the chances of hemorrhage, especially from trauma. The INR in a normal person ranges from 0.8 to 1.2 in an A-Fib patient the INR should be maintained between 2.0 and 3.0 (Avery, et al., *Clin. Pharmacol. Ther.*, 2011).

The inventor has demonstrated that supplementation with t-RES capsules produced improved cognition, speech and movement in a patient with Parkinson's Disease. The inventor's findings further show that t-RES has an effect on neurons expressing proteins, most likely the amyloid-related protein alpha-synuclein, which have been found to be toxic in Parkinson's Disease. The combination of t-RES and reduced more frequent levodopa dosage not only reduces dyskinesia but is likely safer for the patient's brain which may be suffering from free-radical damage thought to be generated from excessive levodopa, shown to be toxic to cultured neurons in the laboratory (Tanaka, et al., *J Neuronal Sci.*, 1991) although a clinical trial showed no damage to nigral neurons (Agid, et al., *Mov. Disord.*, 1999). While a recent study on pathology samples showed no visible levodopa damage on neuronal specimens from patients taking high levels of levodopa for an extended period (Parkinnen, et al., *Neurology*. 2011) levodopa still contributes to neuronal challenges as evidenced by dyskinesias (LeWitt, et al., *Neurology*, 2011). The potential preventive and neuroprotective role of t-RES is emphasized by the earlier finding that the MAO-B inhibitor deprenyl was shown to extend the lifespan of some patients by up to 10 years.

Other benefits were also shown, such as a decrease in punding (repeated activities) and a general improvement of mood. The inventor has had the benefit of observing the patient closely over an eight-year period and demonstrated the essential benefits of a clear visual field and ordered environment and appropriate environmental colors on patient health and the foreseeable fall-risks which can accompany compulsive behavior in administering dopaminergic drugs such as SINEMET®, and MAO inhibitors. The inventor, thus, has demonstrated the use of t-RES as an adjunct treatment for the symptoms of Parkinson's Disease apparently through a similar mechanism to MAO-B inhibitors.

These findings, specifically immediate and progressive improvement in the patient's functioning and reduced need for carbidopa/levodopa, suggest that t-RES may be used as an effective additional therapeutic agent for PD patients (as well as Parkinson's Disease patients with Alzheimer's Disease-like symptoms) and other diseases such as Alzheimer's Disease and Huntingdon's Disease. Importantly, these findings have important implications for military personnel who may have suffered traumatic brain injury, post-traumatic stress disorder, concussions and/or exposure to toxins which have been shown to increase the probability of dementia, Parkinson's Disease and Alzheimer's Disease.

EXAMPLES

In a particular embodiment, the effect of t-RES on a 75 year old female patient with stage four idiopathic Parkinson's Disease was observed. The patient was followed closely for fourteen months while receiving t-RES. t-RES was administered daily and changes in speech, handwriting, gait, leg movement, and dyskinesias were observed. Primary outcome measures were discernible and measurable improvements in cognition and functioning and the presence of dyskinesias were observed. Results were measured by daily observation of changes in functioning, monitoring of dyskinesias, and tolerance of resveratrol and carbidopa/levodopa. Handwriting samples were taken before and after taking t-RES.

The patient was given a starting dose of one capsule of t-RES as the proprietary extract blend ResVinol™ from Red Wine Matrix (*Vitis vinefera*) and *Polygonum cuspidatum* root providing 125 mg trans-Resveratrol and 100 mg Red Wine Polyphenols per capsule (Walgreens, Finest Natural, Triple Strength formulation, distributed by Walgreen Co., 200 Wilmot Rd., Deerfield, Ill. 60015). ResVinol™ comprises about 25% Resveratrol and about 20% Red Wine polyphenols. Starting dose of ½ pill 3 times/day SINEMET® 25/100 and 4 pills/day SINEMET® CR 25/100. Doses were given every four hours starting at 7 am.

Doses of SINEMET® and SINEMET® CR given to the patient were progressively reduced upon the administration of trans-resveratrol (t-RES). Patient had previously been and continued taking: capsules daily BRAIN SUSTAIN® combination: magnesium citrate (30 mg/capsule), N-acetyl-L-cysteine (100 mg/capsule) (Pahan, et al., *Free Radical Biology and Medicine*, 1998), phosphatidylserine (25 mg/capsule) (Crook, et al., *Neurology*, 1991), acetyl-L-carnitine (100 mg/capsule), (Steffen, et al., *Human Exp. Toxicol*, 1995; and Thal, et al., *Neurology*, 1996) alpha lipoic acid (25 mg/capsule), (Marangon, et al., *Free Radical Biology and Medicine*, 1999), CoEnzyme Q10 (25 mg/capsule, total 1200 mg CoQ10/day) (Shults, et al., *Arch Neurol.*, 2002) (Dr. Perlmutter's, Neuroactives Brain Sustain Tier 3 (Xymogen), and 1.25 mg melatonin/night, shown to potentiate the neuroprotective properties of resveratrol in mice (Kwon, et al., *J. Clin. Neurol.*, 2010). and 5 ml glutathione (READISORB®) diluted to 100 ml in orange juice taken twice daily on an empty stomach.

Following the administration of t-RES, the patient exhibited an overnight improvement in cognition and speech. Prior to taking t-RES, the patient had been unable to finish sentences, lacked any dyskinesias, had regular hallucinations, an increasing need for SINEMET®, and progressively poor gait with stooped posture and weakness. Progressive improvements in all areas, particularly speech and cognition initially, were accompanied by increased dyskinesias and a reduced need for SINEMET®. Improvements continued for about two months followed by a plateau.

Following plateaus, as evidenced by decreased response to SINEMET®, t-RES was increased by 125 mg/day roughly every two to three months to a dose of 625 mg t-RES and 500 mg polyphenols in 1-2 capsules given every four hours per day without food, which may be switched to a more expensive liquid form if swallowing becomes intolerable. Eleven months into the study, patient was taking 500 mg t-RES/day, considered the lowest mega-dose, plus the added 100 mg general polyphenols which are mixed into each 125 mg t-RES capsule. 5000 mg of t-RES per day has been shown to cause no adverse effects in healthy volunteers (Boocock, et al., *Cancer Epidemiology, Biomarkers & Prevention,* 2007).

Upon initial administration of resveratrol, dyskinesias became pronounced necessitating a reduction Sinemet 25/100 to ¼ pill three to four times daily, from ½ pill thrice daily in the first few days of t-RES administration. A gradual substitution of SINEMET® CR to SINEMET®, from four SINEMET® CR pills daily to one CR pill daily over six months, eliminating SINEMET® CR entirely after 10 months, was required to reduce dyskinesias. Elimination of the SINEMET® CR form produced an unexpected reduction in patient's anxiety, which had appeared to coincide with the "wearing off" or increasing tremor state. The patient had responded better to the SINEMET® CR form than the regular form of Sinemet for the first 19 years of her Parkinson's Disease, as SINEMET® in a non-CR form tended to enter the system too quickly, producing disabling dyskinesias and hallucinations, particularly after 7 pm. This is consistent with the reduced prevalence of motor fluctuations and dyskinesia after 5 years of levodopa treatment in the SINEMET® CR First and similar studies (Block, et al., *Eur. Neurol.,* 1997; and Koller, et al., *Neurology,* 1999). 20 years into the disease, however, the SINEMET® CR form did not enter the system quickly enough and built up to produce dyskinesias at unpredictable times, increasing the likelihood of falling, particularly as the patient is often unaware that she is experiencing dyskinesia. Both forms of SINEMET® are aided in their action by t-RES, however.

Mild dyskinesias were still occurring after 11 months on t-RES, generally at 12 pm and 5:30 pm, and SINEMET® CR was no longer given. Hallucinations were completely eliminated on most days soon after beginning the t-RES, possibly due to its antidepressant properties (Xu, et al., *Eur Neuropsychopharmacol.* 2010), following the initial finding in rat brain that it could serve as an antidepressant template based on its ability to inhibit MAO-A slightly more than MAO-B (Yáñez, et al., *Biochem Biosphys Res. Commun.* 2006) and the reduced need for Sinemet. MAO-B inhibitors such as selegiline are generally recommended in the early stages of PD to forestall the use of levodopa (Hauser, R. A., *Am. J. Manag. Care.,* 2010). The inventor, however, has demonstrated that, unexpectedly, t-RES, which is an MAO inhibitor, can successfully be used to treat even late stage patients to lengthen the period of effectiveness of levodopa. Specifically, 14 months after the first t-RES dose, few hallucinations were evident; however, the patient became confused more often, but had a generally stable cognitive state.

Reducing glutathione produced a worsening of symptoms, with increased tremor, weakness and anxiety being most evident. Blood coagulation on 500 mg followed by 625 mg t-RES was also measured using a standard INR test ordered along with a complete blood count by the patient's Internist eight and 12 months into the study and was found to be normal with a score of 1 in a normal range of 0.8-1.2 with normal readings in all other categories apart from very slight elevations in LDL cholesterol. Kidney function also tested within the normal range (data not shown).

Figure 1:
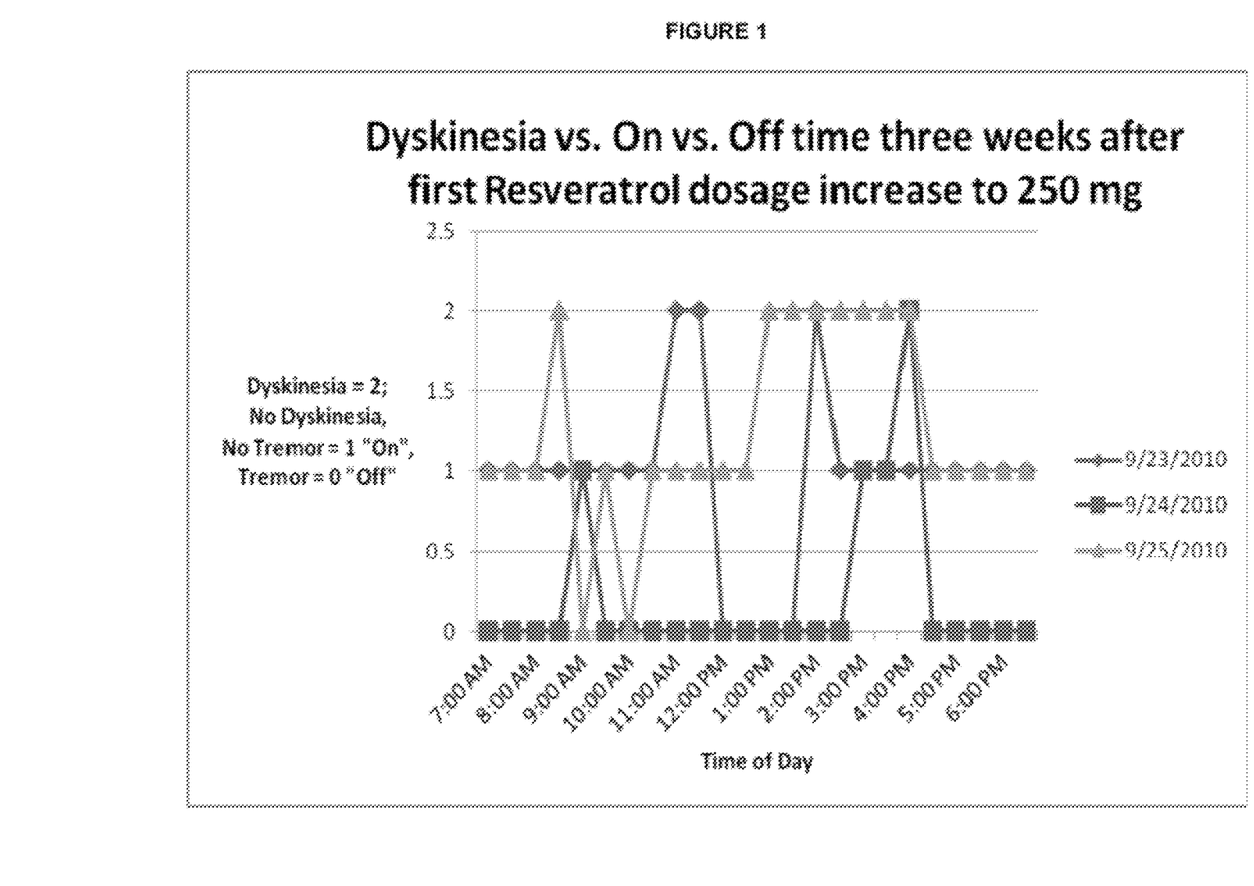
FIG. 1 shows effect of resveratrol on SINEMET®'s action in a patient suffering from Parkinson's Disease.

From the beginning of t-RES administration, an interaction was noted with the SINEMET® that required a reduction in the SINEMET® dose to reduce the dyskinesias which appeared. The t-RES appeared to enhance the SINEMET®'s action, thus requiring less of it to be administered (FIG. 1). The patient's on/off state was monitored every half-hour shortly after dyskinesias became present in an effort to reduce the patient's "off" (tremor) and dyskinesia (overmedicated) time and maximize the patient's "on" (non-tremor/non-dyskinesia) time. This was achieved using a scale devised by the inventor, with three states: tremor, no dyskinesia (T, ND=0); non-tremor, no dyskinesia (NT, ND=1); and dyskinesia, no tremor (D, NT=2). The patient's state was recorded every half hour from 7 am to 10 pm by the author and caregivers on all days practicable.

Patients on the anticoagulant warfarin are expected to have a reading between 2 and 3, with three being the least coagulated. Patient INR readings on t-RES were consistently within the normal range (Table 2). Thus, fall-risk patients need not fear taking t-RES for its excessive anticoagulant properties. Indeed, t-RES appears to sufficiently, but not excessively, thin the blood as is often the case with aspirin, warfarin and even fish oil in sensitive patients. In fact, it appears to be a gentler substitute for more anticoagulating substances such as aspirin and fish oil, which produced mild surface hematomas in this patient when the patient was taking 250 mg t-RES two months after beginning t-RES, when the attending emergency room (ER) physician recommended removing aspirin from the patient's regime, even though an ER blood test revealed an INR of 1, within the normal range (data not shown).

Notably, following the removal of 81 mg aspirin from the patient's daily pill schedule reduced the patient's susceptibility to bruising. The patient was still taking 1000 mg of flaxseed oil per day, which is converted to Omega-3 in the body as the patient's susceptibility to bruising was also excessive on 1000 mg/day of fish oil. In a 23andMe® genetic analysis taken in 2009 under the company's PD $25 per patient test, the patient revealed a genetic sensitivity for warfarin and other anti-coagulants as well as no known genetic markers for Parkinson's Disease. This may explain in part the severe complications the patient suffered after a fall while on warfarin.

TABLE 2

Effect of 500 mg and 625 of t-RES on International Normalized Ratio (INR) reading

| Component | Latest Ref. Range | Jul. 6, 2011 (625 mg t-Res) | Mar. 14, 2011 (500 mg t-Res) | Oct. 26, 2010 (250 mg t-Res + 81 mg/day aspirin) |
|---|---|---|---|---|
| INR | 0.8-1.2 | 1.0 | 1.0 | 1.0 |

The advantage of recording tremor data every half hour was to allow optimal adjustment of the SINEMET® dosage and to visualize the effect of the t-RES on the SINEMET®. Prior to taking t-RES, the patient was taking one SINEMET® CR every four hours from 7 am to 7 pm and ½ SINEMET® at 7 am, 11 am and 3 pm. At fourteen months into the study, the current dosage schedule requires cutting the un-scored name-brand pills to ½ SINEMET® at 7, 9, 10, and 11 am, 2, 3, 5 and 7:30 pm in addition to giving ¼ SINEMET® at 12, 4, 7:30 and 9 pm on cold and/or cloudy days (when atmospheric pressure is lower) and days when the patient swims, adding another ¼ at 12 and 4, if excessive tremor is present as activity uses SINEMET® faster. Patient's mealtimes were at 8 am, 1 pm and 6 pm and SINEMET® was not administered an hour before or an hour after finishing meals. On sunny days (when atmospheric pressure is higher), the patient generally has to decrease the 12 pm dose to ¼ pill or remove it, due to disabling dyskinesias in addition to reducing or eliminating the 4 pm dose (Table 3). Avoiding SINEMET® an hour before or after food was shown to be very important in maximizing SINEMET® absorption, although ¼ SINEMET® is given with food if patient begins to tremor, an unusual occurrence.

An effective daily dose of resveratrol is in the range of about 100 mg to about 1000 mg, which in some embodiments includes polyphenols, such as regimen of 100 mg polyphenols/125 mg trans-resveratrol/capsules, spread out to 125-250 mg t-RES. The t-RES can be given with 50 mg levodopa every four hours without food generally beginning in the morning. Additional 25-50 mg doses of levodopa may be given hourly (except for mealtimes), for a total of about 150-750 mg levodopa/day (see, e.g., Table 3), for example about 250-500 levodopa/day. The starting dose may be lowered for earlier stage patients and, in one embodiment, only be 125 mg maximum t-RES until dyskinetic effects are reduced and a workable t-RES/levodopa dose is reached. Once these issues have been resolved, in particular embodiments, the dosage of t-RES may be about 50, 60, 75, 100, 150, 200, 250, 300, 350, 400, 450, 500, 550, 500, 625 mg/day, 650, 700, 750, 800, 850, or 900 mg/day, and the dosage of levodopa may be about 150, 200, 250, 300, 350, 400, 450, 500, 550, 600, 650, 700, or 750 mg/day.

In on embodiment, T-RES plateaus occurs roughly every eight weeks, which may necessitate an increase in the t-RES dosage. Other patients may need larger doses of t-RES and/or levodopa, and since t-RES has been shown to be safe in healthy volunteers up to 5000 mg, a dose range up to that level may be tolerable, taking the concomitant dosage of levodopa into account.

TABLE 3

SINEMET ® dosage schedule before and 14 months after beginning treatment with t-RES

| Time | Sinemet STD before t-RES (July 2010) | Sinemet CR before t-RES (July 2010) | Sinemet STD, 14 months post t-RES (625 mg/day) (September 2011) | Supplement dosage 14 months post-t-RES (September 2011) |
|---|---|---|---|---|
| 7.00 am | ½ pill (12.5 mg carbidopa(C)/50 mg levodopa (L)) | 1 pill (25 mg C/100 mg L) | ½ pill (12.5 mg C/50 mg L) | 125 mg t-RES/100 mg polyphenols |
| 7.30 am | | | | |
| 8.00 am | | | breakfast | |
| 8.30 am | | | | |
| 9.00 am | | | ½ pill (or 45 min. after finishing breakfast) (12.5 mg C/50 mg L) | |
| 9.30 am | | | | |
| 10.00 am | | | ½ pill (12.5 mg C/50 mg L) | |
| 10.30 am | | | | |
| 11.00 am | ½ pill (12.5 mg C/50 mg L) | 1 pill (25 mg C/100 mg L) | ½ pill (12.5 mg C/50 mg L) | 125 mg t-RES/100 mg polyphenols |
| 11.30 am | | | | |
| 12.00 pm | | | ¼ pill; none if dyskinesia; ½ if tremor (6.25 mg C/25 mg L-12.5 mg C/50 mg L) | |
| 12.30 pm | | | | |
| 1.00 pm | | | lunch | |
| 1.30 pm | | | | |
| 2.00 pm | | | ¼ pill; none if excessive dyskinesia (12.5 mg C/25 mg L) | |
| 2.30 pm | | | | |
| 3.00 pm | ½ pill (12.5 mg C/50 mg L) | 1 pill (25 mg C/100 mg L) | ½ pill (12.5 mg C/50 mg L) | 250 mg RES/200 mg polyphenols |
| 3.30 pm | | | | |
| 4.00 pm | | | ¼ pill; none if dyskinesia; ½ if tremor (6.25 mg C/25 mg L to 12.5 mg C/50 mg L) | |
| 4.30 pm | | | | |
| 5.00 pm | | | ½ pill (12.5 mg C/50 mg L) | |
| 5.30 pm | | | | |
| 6.00 pm | | | dinner | |
| 6.30 pm | | | | |
| 7.00 pm | | 1 pill (25 mg C/100 mg L) | | 250 mg RES/200 mg polyphenols |

TABLE 3-continued

SINEMET® dosage schedule before and 14 months after beginning treatment with t-RES

| Time | Sinemet STD before t-RES (July 2010) | Sinemet CR before t-RES (July 2010) | Sinemet STD, 14 months post t-RES (625 mg/day) (September 2011) | Supplement dosage 14 months post-t-RES (September 2011) |
|---|---|---|---|---|
| 7.30 pm | | | ½ + ¼ pill (25-50 mg L) | |
| 8.00 pm | | | | |
| 8.30 pm | | | | |
| 9.00 pm | | Total Levodopa per day = 550 mg | ¼ pill unless dyskinesia (6.25 mg C/25 mg L) | Total Levodopa per day = 500 mg max |

Figure 2:
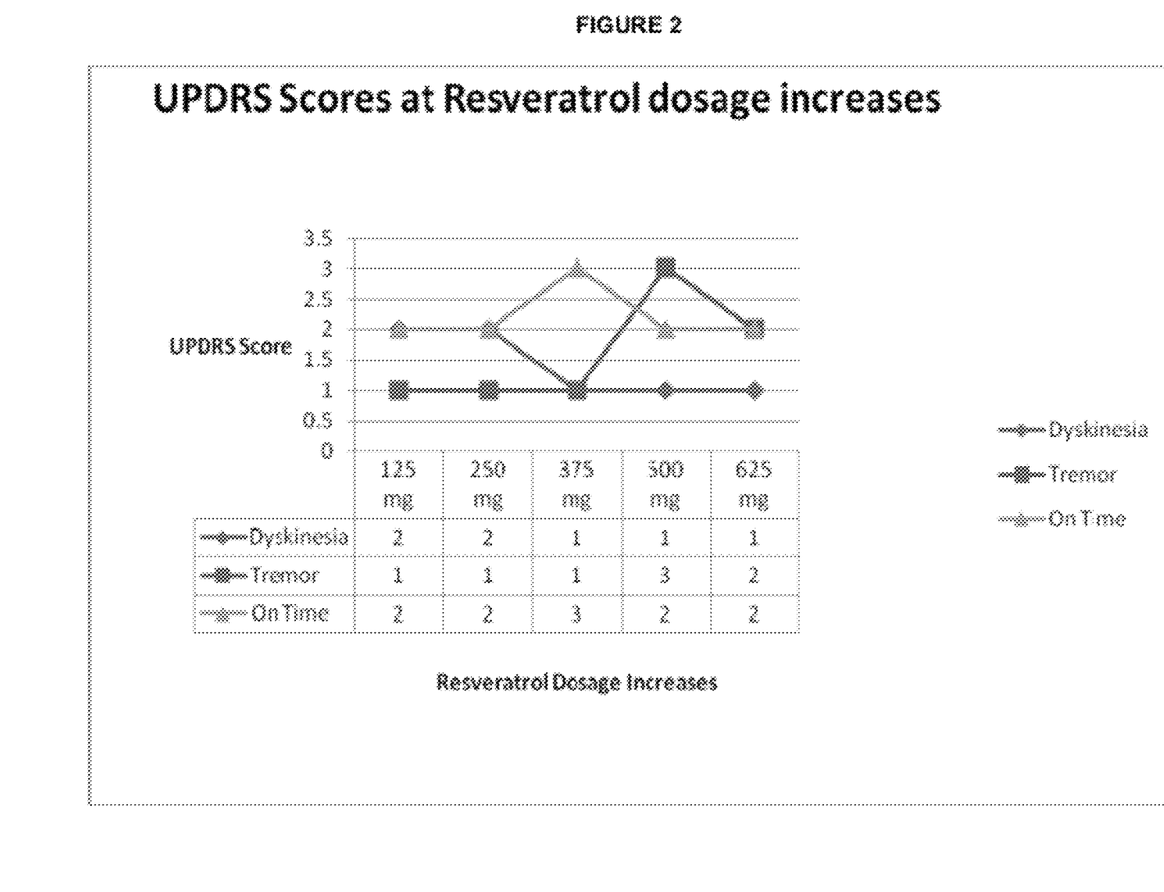
FIG. 2 shows the effect of resveratrol on a patient suffering from Parkinson's Disease. Based on the Unified Parkinson's Disease Rating Scale (UPDRS), which is a rating scale used to follow the longitudinal course of Parkinson's Disease, the patient's tremors and dyskinesias rarely occurred over 25% of the day and patient's "on" time (not measured by the UPDRS, but included as a new UPDRS variable by the inventor) was usually 75% of the day. The figure illustrates levels at trans-resveratrol dosage increase points.

Daily numbers from the inventor's 0-2 Tremor Rating Scale (TRS) scale were then tallied and entered into the Unified Parkinson's Disease Rating Scale (UPDRS) for comparison. Based on UPDRS ratings, the patient's tremors and dyskinesias rarely occurred over 25% of the day and patient's "on" time (not measured by the UPDRS, but included as a new UPDRS variable by the author) was usually 75% of the day as shown in FIG. 2.

Shulman et al. has reported that the UPDRS only provided a gross measure of a patient's overall "on/off" state (Shulman, et al., Arch. Neural., 2010). This problem is addressed well by the inventor's 0-2 scale which allows a refined look into the half-hourly trends in on/off state by the patient and provides a useful guideline for physicians who may want to safely recommend t-RES to their patients and a safe t-RES/SINEMET® dosage regime in general for other potential pharmacologic formulations using t-RES.

Figure 3:
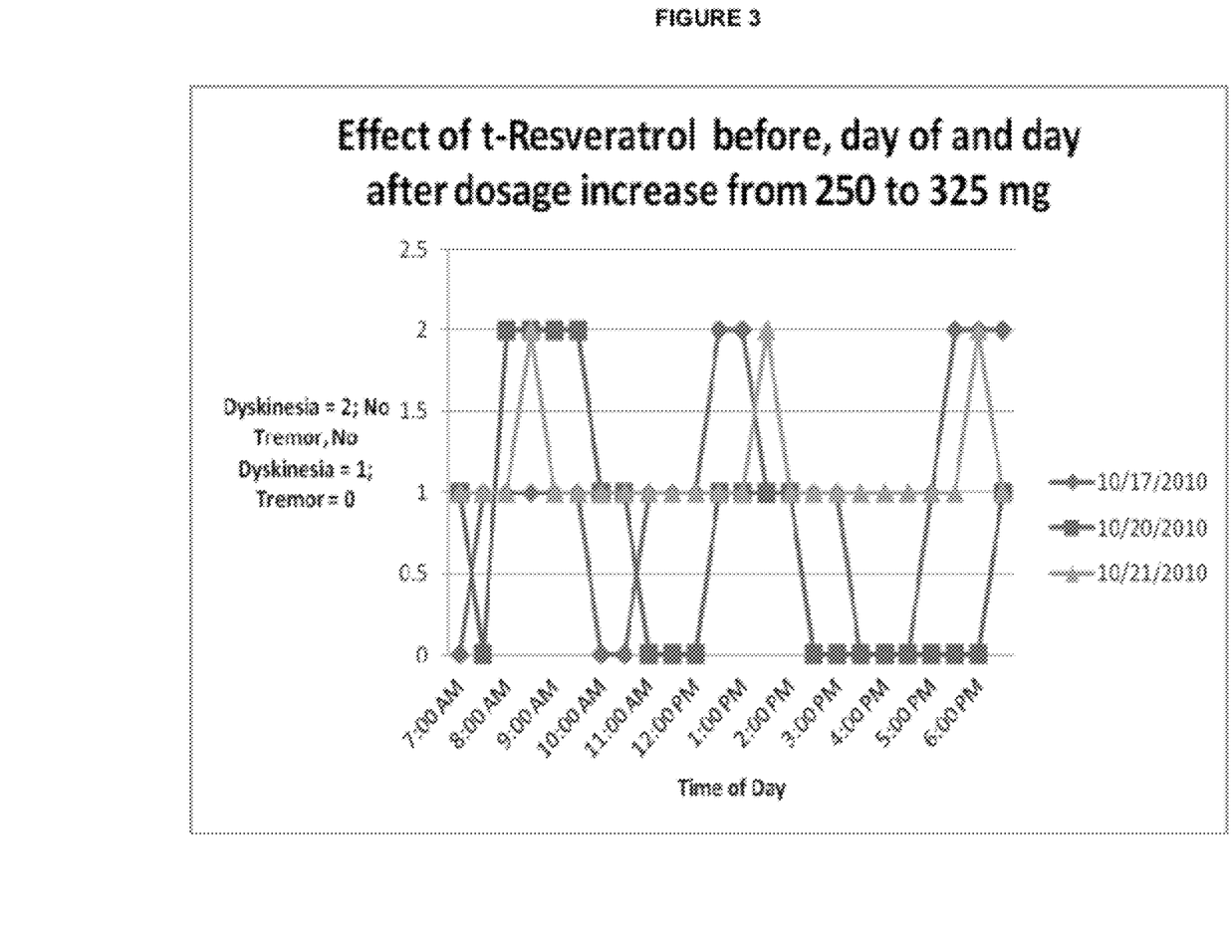
FIG. 3 shows visualization of trans-resveratrol's effect on a patient suffering from Parkinson's Disease, wherein the effect of t-RES was measured several days before, the day of, and day after a trans-resveratrol dose was increased to show the effect of an increase. There is a clear increase in dyskinesias on the day of and day after the resveratrol increase, demonstrating its potentiating effect on Sinemet.

To visualize t-RES's dyskinesiogenic effect, the data sets were divided into one or a few days before, the day of and day after a t-RES dose was increased to show the effect of an increase as shown in FIG. 3. The doses of t-RES, SINEMET® and other supplements were also noted, with adjustments being made as necessary. The results were then examined for overall changes observed when the t-RES dose was increased every few months as shown in FIG. 2. With each increase in t-RES dosage, the patient's dyskinesias increased, requiring less SINEMET®, with a leveling off after about two months, as shown by the t-RES dosage-increase points as shown in FIG. 2. A gradual elimination of SINEMET® CR and replacement of SINEMET® CR with SINEMET® over a period of eight months reduced dyskinesias and their severity as well as the patient's anxiety, which tended to accompany an increasing tremor state.

The maximum SINEMET® dose is normally 4½ to 5½ pills/day (SINEMET® 25/100), with doses rarely exceeding 5½ pills unless pills are given too close to mealtimes or patient when patient is unexpectedly tremoring. To avoid dyskinesias and motor/response fluctuations, ¼ pill is usually the maximum that can be given at 12 pm and 2 pm to prevent disabling dyskinesias which can stop the patient from walking, increase fall-risk and increase disorientation, in addition to being alarming to uninitiated observers.

The inventor has developed a workable regime which kept the patient generally on and free of dyskinesia for about 75% of the day, if administered according to the schedule, with adjustments when necessary. In one embodiment, the timetable generally involves ½ SINEMET® tablet given an hour before and/or after meals and then roughly hourly throughout the day. Between ¼ to ½ SINEMET® pill should be given before a dose wears off entirely to avoid freezing. During clear days, however, some doses could be reduced to ¼ SINEMET® pill or eliminated. Overcast days may increase the need for SINEMET®, evidenced by an increase in time for SINEMET® to take effect.

The inventor has demonstrated that t-RES appears to make SINEMET® act more efficiently, likely acting as an MAO inhibitor to potentiate the action of SINEMET® and thus require less of it.

The improvements seen in the patient are also likely due to the neuroprotective benefits of resveratrol established in a number of previous animal studies. Pool therapy has also improved the patient's overall ability to move, as expected, with an unexpected and surprising transient increase in dyskinesia fourteen months after beginning t-RES.

Importantly, fourteen months after starting t-RES, inadvertent omission of the BRAIN SUSTAIN® supplements from the pill tray for four days, resulted in the patient requiring much more SINEMET®, to avoid tremors, as SINEMET® took longer to act.

As originally observed in 48 months prior to starting t-RES, the BRAIN SUSTAIN® supplements are an important component to the efficient action of the SINEMET®, particularly in cognition. Also of interest are the near perfect readings on the patient's recent standard Complete Blood Count test ordered by the patient's internist (data not shown). These data are in keeping with previous findings which show that t-RES helps normalize a number of bodily systems. At the patient's most recent visit to the neurologist in September 2011, 14 months after starting t-RES, the patient walked into the appointment on a walker, with mild dyskinesias (it was a sunny day), and good cognition. The patient's neurologist of twelve years remarked that the patient was doing remarkably well for someone who has had the condition as long as she has. Taken together, these data demonstrate that t-RES allows SINEMET® to work more efficiently while appearing to slow or possibly reverse the symptoms of Parkinson's Disease.

Glutathione and BRAIN SUSTAIN® also help ameliorate the symptoms of Parkinson's Disease with this patient, however, the t-RES produces the most dramatic improvement as evidenced by increased dyskinesias upon administration of t-RES. The interaction necessitates low doses of SINEMET®, administered at regular intervals to achieve maximum "on" time and minimum dyskinesias.

While the above examples were accomplished with trans-Resveratrol, it is contemplated that similar results could be obtained with cis-Resveratrol and/or an appropriate combination of other polyphenols as were used in the formulation administered.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

REFERENCES

1 The Parkinson Study Group. A controlled trial of rasagiline in early Parkinson disease. The TEMPO study. *Arch Neurol.* 2002, 59(12): 1937-1943.
2 Parkinson Study Group. DATATOP: A multicenter controlled clinical trial in early Parkinson's disease. *Arch Neurol.* 1989; 46:1052-1060.
3 Parkinson Study Group. Effect of Deprenyl on the progression of disability in early Parkinson's disease. *N. Engl. J. Med.* 1989; 321:1364-1371.
4 Mytilineou C, Leonarki E K, Radcliffe P, et al. Deprenyl and desmethylselegiline protect mesencephalic neurons from toxicity induced by glutathione depletion. *J Pharmacol Exp Ther.* 1998:284: 700-706.
5 Tatton W G, Ju W Y, Holland D P, et al. (-)-Deprenyl reduces PC12 cell apoptosis by inducing new protein synthesis. *J Neurochem.* 1994; 63: 1572-1575.
6. Tatton W G, Ju W Y H, Wadia J, et al. Reduction of neuronal apoptosis by small molecules: promise for new approaches to neurological therapy. In: Olanow E W, Jenner P, Youim M H B eds. Neurodegeneration and neuroprotection in Parkinson's Disease. London: Academic Press, 1996: 209-218.
7. Creasy L L, Coffee M. Phytoalexin production potential of grape berries. *J Am Soc Hort Sci* 1988; 113(2):230-234.
8. Karuppagounder S S, Pinto J T, Xu H, Chen H L, Beal M F, Gibson G E. Dietary supplementation with resveratrol reduces plaque pathology in a transgenic model of Alzheimer's disease. *Neurochemistry International* 2009; 54 (2): 111-118.
9. Wood, J G, Rogina, B, Lavu S, Howitz, K, Helfand S L, Tatar, M, Sinclair, D. Sirtuin Activators mimic caloric restriction and delay ageing in metazoans. *Nature.* 2004; 430: 686-89.
10. Kim D, Nguyen M D, Dobbin M M, Fischer A, Sananbenesi F, Rodgers J T, Delalle I, Baur J A, Sui G, Armour S M, Puigserver P, Sinclair D A, Tsai L H. SIRT1 deacetylase protects against neurodegeneration in models for Alzheimer's disease and amyotrophic lateral sclerosis. *EMBO J* 2007; 26(13): 3169-79.
11. Anekonda T S. Resveratrol-a boon for treating Alzheimer's disease? *Brain Research Reviews* 2006; 52: 316-26.
12. Sharma M, Gupta Y K. Chronic treatment with trans-resveratrol prevents intracerebroventricular streptozotocin induced cognitive impairment and oxidative stress in rats. *Life Sciences* 2002; 71: 2489-98.
13. Kumar P, Padi S S, Naidu P S, Kumar A. Effect of resveratrol on 3-nitropropionic acid-induced biochemical and behavioural changes: possible neuroprotective mechanisms. *Behavioural Pharmacology* 2006; 17: 485-92.
14. Yang Y B, Piao Y J. Effects of resveratrol on secondary damages after acute spinal cord injury in rats. *Acta Pharmacologica Sinica* 2003; 24: 703-10.
15. Sinha K, Chaudhary G, Gupta Y K. Protective effect of resveratrol against oxidative stress in middle cerebral artery occlusion model of stroke in rats. *Life Sciences* 2002; 71: 655-65.
16. Yáñez, M, Fraiz, N, Cano, E, Orallo, F Inhibitory effects of cis- and trans-resveratrol on noradrenaline and 5-hydroxytryptamine uptake and on monoamine oxidase activity. *Biochem Biophys Res Commun* 2006; 344: 688-95.
17. Li Y, Grupe A, Rowland C, Holmans P, Segurado R, Abraham R, Jones L, Catanese J, Ross D, Mayo K, Martinez M, Hollingworth P, Goate A, Cairns N J, Racette B A, Perlmutter J S, O'Donovan M C, Morris J C, Brayne C, Rubinsztein D C, Lovestone S, Thal L J, Owen M J and Williams J. Evidence that common variation in NEDD9 is associated with to late-onset Alzheimer's and Parkinson's disease. *Hum Mol Genet* 2008; 17:759-767.
18. Walle T, Hsieh F, DeLegge M H, Oatis J E, Walle U K. High absorption but very low bioavailability of oral resveratrol in humans. *Drug Metabolism and Disposition* 2004; 32: 1377-82.
19. la Porte C, Voduc N, Zhang G, Seguin I, Tardiff D, Singhal N, Cameron D W. Steady-State Pharmacokinetics and Tolerability of Trans-Resveratrol 2000 mg Twice Daily with Food, Quercetin and Alcohol (Ethanol) in Healthy Human Subjects. *Clinical Pharmacokinetics.* 2010; 49: 449-454.
20. Boocock D J, Faust G E, Patel K R, et at Phase I dose escalation pharmacokinetic study in healthy volunteers of resveratrol, a potential cancer chemopreventive agent. *Cancer Epidemiology, Biomarkers & Prevention* 2007; 16: 1246-52.
21. Marier J F, Vachon P, Gritsas A, Zhang J, Moreau J P, Ducharme M P. Metabolism and disposition of resveratrol in rats: extent of absorption, glucuronidation, and enterohepatic recirculation evidenced by a linked-rat model. *The Journal of Pharmacology and Experimental Therapeutics* 2002; 302 (1): 369-73.
22. Abd El-Mohsen M, Bayele H, Kuhnle G, et al. Distribution of [$^3$H]trans-resveratrol in rat tissues following oral administration. *The British Journal of Nutrition* 2006; 96: 62-70.
23. Wenzel E, Soldo T, Erbersdobler H, Somoza V. Bioactivity and metabolism of trans-resveratrol orally administered to Wistar rats. *Molecular Nutrition & Food Research* 2005; 49: 482-94.
24. Yu C, Shin Y G, Chow A, et al. Human, rat, and mouse metabolism of resveratrol. *Pharmaceutical Research* 2002; 19: 1907-14.
25. Wang L X, Heredia A, Song H, et al. Resveratrol glucuronides as the metabolites of resveratrol in humans: characterization, synthesis, and anti-HIV activity. *Journal of Pharmaceutical Sciences* 2004; 93: 2448-57.

26. Elliott P J, Jirousek M. Sirtuins: novel targets for metabolic disease. *Current Opinion in Investigational Drugs* 2008; 9: 371-8.
27. NCT Identifiers: [NCT00920660] and [NCT01262911].
28. Irvine, G B, El-Agnaf, O M, Shankar, G M, and Walsh, D M. Protein Aggregation in the Brain: The Molecular Basis for Alzheimer's and Parkinson's Diseases. *Mol Med* 2008; 14: 451-464.
29. Shults C W. Lewy bodies. *Proc Natl Acad Sci USA.* 2006; 103: 1661-8.
30. Spillantini M G, Crowther R A, Jakes R, Hasegawa M, Goedert M. alphaSynuclein in filamentous inclusions of Lewy bodies from Parkinson's disease and dementia with Lewy bodies. *Proc Natl Acad Sci USA.* 1998; 95:6469-73.
31. Uversky V N, Li J, Bower K, Fink A L. Synergistic effects of pesticides and metals on the fibrillation of alpha-synuclein: implications for Parkinson's disease. *Neurotoxicology* 2002; 23: 527-36.
32. Wood J G, Mirra S S, Pollock N J, Binder L I. Neurofibrillary tangles of Alzheimer disease share antigenic determinants with the axonal microtubule associated protein Tau®. *Proc Natl Acad Aci USA.* 1986; 83:4040-3.
33. Kosik K S, Joachim C L, Selkoe D J. Microtubule-associated protein Tau® is a major antigenic component of paired helical filaments in Alzneimer disease. *Proc Natl Acad Sci USA* 1986; 83: 4044-8.
34. Hutton M, Lendon C L, Rizzu P, Baker M, Froelich S, Houlden H, Pickering-Brown S, Chakraverty S, Issacs A, Grover A, et al. Association of missense and 5'-splice-site mutations in tau with the inherited dementia FTDP-17. *Nature.* 1998; 393:702-705.
35. Gotz J, Chen F, van Dorpe J, Nitsch R M. Formation of neurofibrillary tangles in P301I tau transgenic mice induced by Abeta 42 fibrils. *Science.* 2001; 293: 1491-5.
36. Lewis J, Dickson D W, Lin W L, Chisholm L, Corral A, Jones G, Yen S H, Sahara N, Skipper L, Yager D, Eckman C, Hardy J, Hutton M, McGowan E. Enhanced neurofibrillary degeneration in transgenic mice expressing mutant tau and APP. *Science.* 2001; 293:1487-91.
37. Reifert J, Hartung-Cranston D, Feinstein S C. Amyloid beta mediated cell death of cultured hippocampal cells. *J Biol Chem* 2011; 11:1-26.
38. Morishima-Kawashima M, Hasegawa M, Takio K, Suzuki M, Yoshida H, Watanabe A, Titani K, Ihara Y. Hyperphosphorylation of tau in PHF. *Neurobiol Aging* 1995; 16:365-380.
39. Lee G, Thangavel R, Sharma, V M, Litersky J M, Bhasker K, Fang, S M, Do L H, Andreadis, A, Van Hoesen G, and Ksiezak-Reding H. Phosphorylation of Tau by Fyn: Implications for Alzheimer's Disease. *J Neurosci* 2004; 24:2304-2312.
40. Scales T M E., Derkinderen P, Leung K-Y, Byers H L, Ward M A, Price C, Bird I N, Perera T, Kellie S, Williamson R, Anderton B H, and Reynolds C H. Tyrosine Phosphorylation of Tau by the Src Family Kinases Lck and Fyn. *Mol Neurodegen* 2011; 6:12-36.
41. Lebouvier T, Scales T M, Hanger D P, Geahlen R L, Lardeux B, Reynolds C H, Anderton B H, Derkinderen P. The microtubule-associated protein tau is phosphorylated by Syk. *Biochim Biophy Acta* 2008; 1783:188-192.
42. Derkinderen P, Scales T M, Hanger D P, Leung K Y, Byers H L, Ward M A, Lenz C, Price C, Bird I N, Perera T, Kellie S, Williamson R, Noble W, Van Etten R A, Leroy K, Brion J P, Reynolds C H, Anderton B H. Tyrosine 394 is phosphorylated In Alzheimer's paired helical filament tau and in fetal tau with c-Abl as the candidate tyrosine kinase. *J Neurosci* 2005; 25: 6584-6593.
43. He G, Luo W, Li P, Remmers C, Netzer W J, Hendrick J, Bettayeb K, Flajolet M, Gorelick F, Wennogle L P, Greengard P. Gamma-secretase activating protein is a therapeutic target for Alzheimer's disease. *Nature.* 2010; 467:95-98.
44. Dai H, Marbach P, Lemaire M, Hayes M, Elmquist W F. Distribution of STI-571 to the brain is limited by P-glycoprotein-mediated efflux. *J Pharmacol* Exp Ther 2003; 304: 1085-92.
45. Hollingworth P, et. al., Common variants at ABCA7, MS4A6A/MS4A4E, EPHA1, CD33 and CD2AP are associated with Alzheimer's disease. *Nat Genetics* 2011; 43: 429-434.
46. Naj, A C. Common variants at MS4A4/MS4A6E, CD2AP, CD33 and EPHA1 are associated with late-onset Alzheimer's disease. *Nat Genetics* 2011; 43: 436-441.
47. Andrews R G, Torok-Storb B, Bernstein I D: Myeloid-associated differentiation antigens on stem cells and their progeny identified by monoclonal antibodies. *Blood* 62:124-132, 1983.
48. Griffin J D, Linch D, Sabbath K, Larcom P, Schlossman S F: A monoclonal antibody reactive with normal and leukemic human myeloid progenitor cells. *Leuk Res* 1984; 8:521-34.
49. Freeman S D, Kelm S, Barber, E K, and Crocker P R. Characterisation of CD33 as a new member of the sialoadhesin family of cell adhesion molecules. *Blood* 1995; 85:2005-2012.
50. Barber E K. Chapter 4, CD33 is Phosphorylated in Myeloid Cell Lines. From: Barber E K: A Functional Analysis of CD33 and CD34. (Examined Thesis submitted to Oxford University Library, July, 1997).
51. Taylor V C, Buckley C D, Douglas M, Cody A J, Simmons D L, Freeman S D. The myeloid-specific sialic acid binding receptor, CD33, associates with the protein-tyrosine phosphatases, SHP-1 and SHP-2. *J Biol Chem* 1999; 274:11505-12.
52. Paul S P, Taylor L S, Stansbury E K, and McVicar D W. Myeloid specific human CD33 is an inhibitory receptor with differential ITIM function in recruiting the phosphatases SHP-1 and SHP-2. *Blood* 2000; 96:483-490.
53. Wang J, Santa-Maria I, Ho L, Ksiezak-Reding H, Ono K, Teplow D B, Pasinetti G M. Grape derived polyphenols attenuate tau neuropathology in a mouse model of Alzheimer's disease. J Alzheimers Dis 2010; 22:653-61.
54. Wang Q, Xu J, Rottinghaus G E, Simonyi A, Lubahn D, Sun G Y, Sun A Y. Brain Res. Resveratrol protects against global cerebral ischemic injury in gerbils. 2002; 958: 439-47.
55. Donmez G, Wang D, Cohen D E, Guarente L. SIRT1 suppresses beta-amyloid production by activating the alpha-secretase gene ADAM10. *Cell* 2010; 142:320-332. Erratum in: *Cell* 2010; 142:494-5.
56. Karuppagounder S S, Pinto J T, Xu H, Chen H L, Beal M F and Gibson G E. Dietary supplementation with resveratrol reduces plaque pathology in a transgenic model of Alzheimer's disease. *Neurochem Int* 2009; 54:111-8.
57. Spillantini M G, Crowther R A, Jakes F, Hasegawa M, Goedert M. alpha-Synuclein in filamentous inclusions of Lewy bodies from Parkinson's disease and dementia with Lewy bodies. *Proc Natl Acad Sci USA.* 1998; 95:6469-73.

58. Chen L and Feany M B. a-Synuclein phosphorylation controls neurotoxicity and inclusion formation in a Drosophila model of Parkinson disease. *Nature Neuroscience* 2005; 8: 657-663.
59. Chen L, Periquet M, Wang X, Negro A, McLean P J, Hyman B T, Feany, M B. Tyrosine and serine phosphorylation of alpha-synuclein have opposing effects on neurotoxicity and soluble oligomer formation. *J Clin Invest* 2009; 119:3257-65.
60. Cavallarin N, Vicario M, Negro A. The role of phosphorylation in synucleinopathies: focus on Parkinson's disease. *CNS Neurol Disord Drug Targets.* 2010; 9:471-81.
61. Nakamura T, Yamashita H, Takahashi T and Nakamura S. Activated Fyn Phosphorylates a-Synuclein at Tyrosine Residue 125. *Biochem And Biophys Res Comm* 2001; 280:1085-1092.
62. Negro A, Brunati A M, Donella-Deana A, Massimino M L, Pinna L A. Multiple phosphorylation of alpha-synuclein by protein tyrosine kinase Syk prevents eosin induced aggregation. *FASEB J* 2002; 16:210-2.
63. Nakamura T, Yamashita H, Nagano Y, Takahashi T, Avraham S, Avraham H, Matsumoto M, Nakamura S. Activation of Pyk2/RAFTK induces tyrosine phosphorylation of a-synuclein via Src-family kinases. *FEBS Letts.* 2001; 521:190-194.
64. Montine T J, Shi M, Quinn J F, Peskind E R, Craft S, Ginghina C, Chung K A, Kim H, Galasko D R, Jankovic J, Zabetian C P, Leverenz J B, Zhang J. CSF AP(42) and tau in Parkinson's disease with cognitive impairment. *Mov Disord* 2010; 25:2682-5.
65. Lei P, Ayton S, Finkelstein D I, Adlard P A, Masters C L, Bush A I. Tau protein: relevance to Parkinson's disease. *Int J Biochem Cell Biol.* 2010; 42:1775-8.
66. Williamson R, Scales T, Clark B R, Gibb G, Reynolds C H, Kellie S, Bird I N, Varndell I M, Shepppard P W, Everall I, Anderton B H. Rapid tyrosine phosphorylation of neuronal proteins including tau and focal adhesion kinase in response to amyloid-beta peptide exposure: involvement of Src family protein kinases. *J Neurosci* 2002; 22:10-20.
67. Vega I E, Cui L, Propst J A, Hutton M L, Lee G, Yen S H. Increase in tau tyrosine phosphorylation correlates with the formation of tau aggregates. *Brain Res Mol Brain Res* 2005; 138:135-144.
68. Kode A, Rajendrasozhan S, Caito S, Yang S R, Megson I L, Rahman I. Resveratrol induces glutathione synthesis by activation of Nrf2 and protects against cigarette smoke-mediated oxidative stress in human lung epithelial cells. American Journal of Physiology. *Lung Cellular and Molecular Physiology* 2008; 294: L478-88.
69. Fahn, S, Elton, R, Members of the UPDRS Development Committee. In: Fahn, S, Marsden, C D, Caine, D B, Goldstein, M, eds. Recent Developments in Parkinson's Disease, Vol 2. Florham Park, N.J. Macmillan Health Care Information 1987; pp 153-163, 293-304.
70. Avery P J, Jorgensen A, Hamberg A K, Wadelius M, Pirmohamed M, Kamali F. A proposal for an individualized pharmacogenetics-based warfarin initiation dose regimen for patients commencing anticoagulation therapy. *Clin Pharmacol Ther* 2011; 90:701-6.
71. Sun A Y, Wang Q, Simonyi A and Sun G Y. Resveratrol as a Therapeutic Agent for Neurodegenerative Diseases. *Mol Neurobiol* 2010; 41: 375-83.
72. Baur J A and Sinclair D A. Therapeutic potential of resveratrol: the in vitro evidence. *Nat. Review Drug Discov.* 2006; 5: 493-506.
73. Li Y, Grupe A, Rowland C, et al. Evidence that common variation in NEDD9 is associated with susceptibility to late-onset Alzheimer's and Parkinson's disease. *Hum Mol Genet* 2008; 17: 759-767.
74. Schults C W, Beal M F, Fontaine K, et al. Absorption, tolerability and effects on mitochondrial activity of oral coenzyme Q10 in parkinsonian patients. *Neurology* 1998; 50: 793-795.
75. Tanaka M, Sotomatsu A, Kanal H, et al. Dopa and dopamine cause cultured neuronal death in the presence of iron. *J Neuronal Sci.* 1991; 101: 198-203.
76. Agid Y, Ahlskog E, Albanese A, et al. Levodopa in the treatment of Parkinson's disease. *Mov. Disord.* 1999; 14: 911-913.
77. Parkkinen L, O'Sullivan S S, Kuoppamäki M, et al. Does levodopa accelerate the pathologic process in Parkinson disease brain? Neurology 2011; 77; 1420-1426.
78. LeWitt, Peter A. M D; Dubow, Jordan M D; Singer, Carlos M D. Is levodopa toxic?: Insights from a brain bank. Neurology 2011; 77: 1414-1415.
79. Pahan K, Sheikh G S, Nmboodri A M S, et al. N-acetyl cysteine inhibits induction of NO production by endotoxin or cytokine stimulated rat peritoneal macrophages, C6 glial cells and astrocytes. *Free Rad Biol and Med* 1998; 24: 39-48.
80. Crook T H, Tinkelenberg J, Yesavage J. Effects of phosphatidylserine in age-associated memory impairment. *Neurology* 1991; 41: 644-49.
81. Steffen V, Santiago M, de la Cruz C P, et al. Effect of intraventricular injection of 1-methyl-4-phenylpridinium protection by acetyl-L-carnitine. *Human Exp Toxicol* 1995; 14: 865-871.
82. Thal L J, Carta A, Clarke W R, et al. A 1-year multicenter placebo-controlled study of acetyl-L-carnitine in patients with Alzheimer's disease. *Neurology* 1996; 47: 705-711.
83. Marangon K, Deveraj S, Tirosh O, et al. Comparison of the effect of a-lipoic acid and a-tocopherol supplementation on measures of oxidative stress. *Free Rad Biol and Med* 1999; 27: 1114-1121.
84. Shults C W, Oakes D, Kieburtz K, Beal M F, Haas R, Plumb S, Juncos J L, Nutt J, Shoulson I, Carter J, Kompoliti K, Perlmutter J S, Reich S, Stern M, Watts R L, Kurlan R, Molho E, Harrison M, Lew M. Effects of coenzyme Q10 in early Parkinson disease: evidence of slowing of the functional decline. Parkinson Study Group. *Arch Neurol* 2002; 59:1541-50.
85. Le Bars P, Katz M M, Berman N, et al. A Placebo-Controlled, Double-blind Randomized Trial of an Extract of Gingko Biloba for Dementia, *JAMA* 1997; 278: 1327-32.
86. Kwon K J, Kim H J, Shin C Y, Han S H. Melatonin Potentiates the Neuroprotective Properties of Resveratrol Against Beta-Amyloid-Induced Neurodegeneration by Modulating AMP-Activated Protein Kinase Pathways. *J Clin Neurol* 2010; 6:127-37.
87. Block G, Liss C, Reines S, et al. Comparison of immediate release and controlled release carbidopa/levodopa in Parkinson's Disease. A multicenter 5-year study. The CR First Study Group. *Eur Neurol* 1997; 37: 23-27.
88. Koller W C, Hutton J T, Tolosa E, et al. Immediate-release and controlled release carbidopa/levodopa in PD: a 5-year randomized multicenter study. *Neurology* 1999; 53: 1012-1019.
89. Xu Y, Wang Z, You W, Zhang X, Li S, Barish P A, Vernon M M, Du X, Li G, Pan J, Ogle W O. Antidepressant-like effect of trans-resveratrol: Involvement of serotonin and noradrenaline system. *Eur Neuropsychopharmacol* 2010; 20:405-13.
90. Hauser R A. Early pharmacologic treatment in Parkinson's disease. *Am J Manag Care* 2010; 16: S100-7.
91. Shulman, L M, Gruber-Baldini, A L, Anderson, K E, Fishman, P S, Reich, S G, and Weiner, W W. The Clinically Important Difference on the Unified Parkinson's Disease Rating Scale. *Arch Neurol* 2010; 67: 64-70.
92. Tanaka M, Sotomatsu A, Kanal H, et al. Dopa and dopamine cause cultured neuronal death in the presence of iron. *J Neuronal Sci* 1991; 101: 198-203.
93. Agid Y, Ahlskog E, Albanese A, et al. Levodopa in the treatment of Parkinson's disease. *Mov Disord* 1999; 14: 911-913.
94. Hauser R Z, Lyons, K E, Pahwa R, Zesiewica T A, Golbe L I. In: Chapter 5: Medications for the Treatment of Parkinson's Disease. From: Parkinson's Disease Questions and Answers, 4$^{th}$ ed. West Palm Beach: Merit Publishing International; 2003: pp. 79-85.
95. Goetz C G, Koller W C, Poewe W, Rascol O, Sampaio C. Management of Parkinson's Disease: An evidence-based review. *Mov Disord* 2002; 17(suppl 4): S1-S166.
96. Goetz C G, Poewe W, Rascol O, Sampaio C. Evidence-based medical review update: Pharmacological and surgical treatments of Parkinson's disease: 2001-2004. *Mov Disord* 2005; 20: 523-539.
97. Moretto A and Colosio C. Biochemical and toxicological evidence of neurological effects of pesticides: the example of Parkinson's disease. *Neurotoxicology* 2011; 32: 383-91.
98. Chiang P K, Lam M A, Luo Y. The many faces of amyloid beta in Alzheimer's disease. *Curr Mol Med* 2008; 8: 580-4.
99. Irvine G B, El-Agnaf O M, Shankar G M, Walsh D M. Protein aggregation in the brain: the molecular basis for Alzheimer's and Parkinson's diseases. *Molecular Medicine* (Cambridge, Mass.) 2008; 14: 451-64.
100. Ferreira S T, Vieira M N, De Felice F G. Soluble protein oligomers as emerging toxins in Alzheimer's and other amyloid diseases. *IUBMB Life* 2007; 59: 332-45.
101. Haataja L, Gurlo T, Huang C J, Butler P C. Islet amyloid in type 2 diabetes, and the toxic oligomer hypothesis. *Endocrine Reviews* 2008; 29: 303-16.
102. Höppener J W, Ahrén B, Lips C J. Islet amyloid and type 2 diabetes mellitus. *NEJM* 2000; 343: 411-9.
103. Irvine G B, El-Agnaf O M, Shankar G M, Walsh D M. Protein aggregation in the brain: the molecular basis for Alzheimer's and Parkinson's diseases. *Molecular Medicine* (Cambridge, Mass.) 2008; 14: 451-64.
104. More than just mad cow disease, *Nature Structural Biology* 2001; 8: 281.
105. Truant R, Atwal R S, Desmond C, Munsie L, Tran T. Huntington's disease: revisiting the aggregation hypothesis in polyglutamine neurodegenerative diseases. *The FEBS J* 2008; 275: 4252-62.
106. Weydt P, La Spada A R. Targeting protein aggregation in neurodegeneration—lessons from polyglutamine disorders. *Exp Op on Ther Tar* 2006; 10: 505-13.
107. Speranza V D. Amyloid. From: Baethge B A and Jacobsen D R, Amyloidosis. In: Histologic Preparations. Common Problems and their Solutions, Brown RX ed. National Society of Histotechnology/CAP, 2009.
108. Dotti C G and De Strooper B. Alzheimer's dementia by circulation disorders: when trees hide the forest. *Nat Cell Biol* 2009; 11: 114-6.
109. Sipe J D, Benson M D, Buxbaum J N, et al. Amyloid fibril protein nomenclature: 2010 recommendations from the nomenclature committee of the International Society of Amyloidosis. *Amyloid* 2010; 17: 101-104.

What is claimed is:

1. A method of treating a patient with Parkinson's Disease receiving levodopa therapy, comprising administering to said patient polyphenols comprising t-resveratrol and red wine polyphenols in a ratio of about 125 mg of t-resveratrol to about 100 mg red wine polyphenols in an amount effective to improve at least one of bradykinesia and cognition in said patient, wherein said effective amount of t-resveratrol and red wine polyphenols is from about 125 mg/day resveratrol and 100 mg/day red wine polyphenols to about 5000 mg/day t-resveratrol and 4000 mg/day red wine polyphenols.

2. The method of claim 1, further comprising administering an effective amount of glutathione to the patient.

3. The method of claim 2, further comprising administering to said patient an effective amount of at least one of magnesium citrate, N-acetyl-L-cysteine, phosphatidylserine, acetyl-L-carnitine, alpha-lipoic acid and CoEnzymeQ10.

* * * * *